United States Patent
Xu et al.

(10) Patent No.: US 11,246,994 B2
(45) Date of Patent: Feb. 15, 2022

(54) METHODS FOR INTRODUCTION OF FLOWABLE ACELLULAR TISSUE MATRIX PRODUCTS INTO A HAND

(71) Applicant: LifeCell Corporation, Madison, NJ (US)

(72) Inventors: Hui Xu, Plainsboro, NJ (US); Hui Li, Cranbury, NJ (US); Ming F. Pomerleau, Califon, NJ (US); Darin Messina, Branchburg, NJ (US)

(73) Assignee: LifeCell Corporation, Madison, NJ (US)

( * ) Notice: Subject to any disclaimer, the term of this patent is extended or adjusted under 35 U.S.C. 154(b) by 0 days.

(21) Appl. No.: 16/712,364

(22) Filed: Dec. 12, 2019

(65) Prior Publication Data
US 2020/0114091 A1   Apr. 16, 2020

Related U.S. Application Data

(63) Continuation-in-part of application No. 16/164,975, filed on Oct. 19, 2018.

(60) Provisional application No. 62/574,678, filed on Oct. 19, 2017.

(51) Int. Cl.
*A61M 5/32*   (2006.01)
*A61K 47/36*   (2006.01)
*A61K 35/12*   (2015.01)

(52) U.S. Cl.
CPC ........... *A61M 5/3286* (2013.01); *A61K 35/12* (2013.01); *A61K 47/36* (2013.01)

(58) Field of Classification Search
None
See application file for complete search history.

(56) References Cited

U.S. PATENT DOCUMENTS

| | | |
|---|---|---|
| 4,233,969 A | 11/1980 | Lock et al. |
| 4,373,519 A | 2/1983 | Errede et al. |
| 4,569,348 A | 2/1986 | Hasslinger |
| 4,582,640 A | 4/1986 | Smestad et al. |
| 4,703,108 A | 10/1987 | Silver et al. |
| 4,851,521 A | 7/1989 | della Valle et al. |
| 4,902,508 A | 2/1990 | Badylak et al. |
| 4,950,483 A | 8/1990 | Ksander et al. |

(Continued)

FOREIGN PATENT DOCUMENTS

| | | | |
|---|---|---|---|
| CA | 2905371 C | * 8/2016 | ............ A61L 27/20 |
| EP | 1683417 A1 | 7/2006 | |

(Continued)

OTHER PUBLICATIONS

Ahn et al., The past, present, and future of xenotransplantation. Yonsei Med J. Dec. 31, 2004;45(6):1017-24.

(Continued)

*Primary Examiner* — Quanglong N Truong
(74) *Attorney, Agent, or Firm* — McCarter & English, LLP

(57) ABSTRACT

Tissue product compositions and methods for treating a patient are provided. The tissue product composition may include a flowable carrier including a hyaluronic acid based material and acellular tissue matrix particles mixed within the carrier. Methods of producing the tissue product composition and an injection device filled with the tissue product composition are also provided. Methods of treating a hand of a patient are also provided.

15 Claims, 18 Drawing Sheets

(56) References Cited

U.S. PATENT DOCUMENTS

| | | |
|---|---|---|
| 4,969,912 A | 11/1990 | Kelman et al. |
| 5,024,841 A | 6/1991 | Chu et al. |
| 5,104,957 A | 4/1992 | Kelman et al. |
| 5,131,850 A | 7/1992 | Brockbank |
| 5,149,331 A | 9/1992 | Ferdman et al. |
| 5,160,313 A | 11/1992 | Carpenter et al. |
| 5,231,169 A | 7/1993 | Constantz et al. |
| 5,254,133 A | 10/1993 | Seid |
| 5,263,971 A | 11/1993 | Hirshowitz et al. |
| 5,275,826 A | 1/1994 | Badylak et al. |
| 5,284,655 A | 2/1994 | Bogdansky et al. |
| 5,298,015 A | 3/1994 | Komatsuzaki et al. |
| 5,332,802 A | 7/1994 | Kelman et al. |
| 5,332,804 A | 7/1994 | Florkiewicz et al. |
| 5,336,616 A | 8/1994 | Livesey et al. |
| 5,364,756 A | 11/1994 | Livesey et al. |
| 5,437,651 A | 8/1995 | Todd et al. |
| 5,489,304 A | 2/1996 | Orgill et al. |
| 5,549,584 A | 8/1996 | Gross |
| 5,613,982 A | 3/1997 | Goldstein |
| 5,622,867 A | 4/1997 | Livesey et al. |
| 5,632,778 A | 5/1997 | Goldstein |
| 5,636,643 A | 6/1997 | Argenta et al. |
| 5,641,518 A | 6/1997 | Badylak et al. |
| 5,644,049 A | 7/1997 | Giusti et al. |
| 5,645,081 A | 7/1997 | Argenta et al. |
| 5,712,252 A | 1/1998 | Smith |
| 5,728,752 A | 3/1998 | Scopelianos et al. |
| 5,739,176 A | 4/1998 | Dunn et al. |
| 5,834,232 A | 11/1998 | Bishop et al. |
| 5,993,844 A | 11/1999 | Abraham et al. |
| 6,027,743 A | 2/2000 | Khouri et al. |
| 6,071,267 A | 6/2000 | Zamierowski |
| 6,096,347 A | 8/2000 | Geddes et al. |
| 6,135,116 A | 10/2000 | Vogel et al. |
| 6,179,872 B1 | 1/2001 | Bell et al. |
| 6,194,136 B1 | 2/2001 | Livesey et al. |
| 6,326,018 B1 | 12/2001 | Gertzman et al. |
| 6,345,623 B1 | 2/2002 | Heaton et al. |
| 6,371,992 B1 | 4/2002 | Tanagho et al. |
| 6,432,710 B1 | 8/2002 | Boss, Jr. et al. |
| 6,485,723 B1 | 11/2002 | Badylak et al. |
| 6,553,998 B2 | 4/2003 | Heaton et al. |
| 6,576,265 B1 | 6/2003 | Spievack |
| 6,599,318 B1 | 7/2003 | Gabbay |
| 6,613,278 B1 | 9/2003 | Mills et al. |
| 6,666,892 B2 | 12/2003 | Hiles et al. |
| 6,814,079 B2 | 11/2004 | Heaton et al. |
| 6,840,960 B2 | 1/2005 | Bubb |
| 6,933,326 B1 | 8/2005 | Griffey et al. |
| 6,998,418 B1 | 2/2006 | Sung et al. |
| 7,070,584 B2 | 7/2006 | Johnson et al. |
| 7,153,518 B2 | 12/2006 | Wironen et al. |
| 7,198,046 B1 | 4/2007 | Argenta et al. |
| 7,358,284 B2 | 4/2008 | Griffey et al. |
| 7,425,322 B2 | 9/2008 | Cohn et al. |
| 7,498,040 B2 | 3/2009 | Masinaei et al. |
| 7,498,041 B2 | 3/2009 | Masinaei et al. |
| 7,700,819 B2 | 4/2010 | Ambrosio et al. |
| 7,763,769 B2 | 7/2010 | Johnson et al. |
| 7,799,767 B2 | 9/2010 | Lamberti et al. |
| 7,838,021 B2 | 11/2010 | Lafont et al. |
| 8,067,149 B2 | 11/2011 | Livesey et al. |
| 8,110,216 B2 | 2/2012 | Ambrosio et al. |
| 8,152,783 B2 | 4/2012 | Swain |
| 8,163,974 B2 | 4/2012 | Ambrosio et al. |
| 8,197,551 B2 | 6/2012 | Swain et al. |
| 8,197,806 B2 | 6/2012 | Girouard et al. |
| 8,257,372 B2 | 9/2012 | Swain et al. |
| 8,267,918 B2 | 9/2012 | Johnson et al. |
| 8,324,449 B2 | 12/2012 | McQuillan et al. |
| 9,375,513 B2 | 6/2016 | Sun et al. |
| 9,532,863 B2 | 1/2017 | Hayzlett |
| 9,782,436 B2 | 10/2017 | Sun |
| 10,314,861 B2 | 6/2019 | Sun |
| 2002/0103542 A1 | 8/2002 | Bilbo |
| 2002/0120185 A1 | 8/2002 | Johnson |
| 2002/0193448 A1 | 12/2002 | Wallace et al. |
| 2003/0035843 A1 | 2/2003 | Livesey et al. |
| 2003/0039678 A1 | 2/2003 | Stone et al. |
| 2003/0104026 A1 | 6/2003 | Wironen et al. |
| 2003/0143207 A1 | 7/2003 | Livesey et al. |
| 2003/0225347 A1 | 12/2003 | Argenta et al. |
| 2004/0037735 A1 | 2/2004 | DePaula et al. |
| 2004/0078077 A1 | 4/2004 | Binette et al. |
| 2005/0028228 A1 | 2/2005 | McQuillan et al. |
| 2005/0043819 A1 | 2/2005 | Schmidt et al. |
| 2005/0125077 A1 | 6/2005 | Harmon et al. |
| 2005/0159822 A1 | 7/2005 | Griffey et al. |
| 2005/0260176 A1 | 11/2005 | Ayares et al. |
| 2005/0288796 A1 | 12/2005 | Awad et al. |
| 2006/0058892 A1 | 3/2006 | Lesh et al. |
| 2006/0073592 A1 | 4/2006 | Sun et al. |
| 2006/0127375 A1 | 6/2006 | Livesey et al. |
| 2006/0153816 A1 | 7/2006 | Brown et al. |
| 2006/0210960 A1 | 9/2006 | Livesey et al. |
| 2007/0004961 A1 | 1/2007 | Case et al. |
| 2007/0071729 A1 | 3/2007 | Bernstein |
| 2007/0078522 A2 | 4/2007 | Griffey et al. |
| 2007/0104759 A1 | 5/2007 | Dunn et al. |
| 2007/0219471 A1 | 9/2007 | Johnson et al. |
| 2007/0248575 A1 | 10/2007 | Connor et al. |
| 2008/0027542 A1 | 1/2008 | McQuillan et al. |
| 2008/0027562 A1 | 1/2008 | Fujisato et al. |
| 2008/0114277 A1 | 5/2008 | Ambrosio et al. |
| 2008/0279824 A1 | 11/2008 | Matheny et al. |
| 2009/0024224 A1 | 1/2009 | Chen et al. |
| 2009/0035289 A1 | 2/2009 | Wagner et al. |
| 2009/0157017 A1 | 6/2009 | Ambrosio |
| 2009/0198167 A1 | 8/2009 | Ambrosio |
| 2009/0220579 A1 | 9/2009 | Hassingboe et al. |
| 2009/0287181 A1 | 11/2009 | Kagan |
| 2009/0306790 A1 | 12/2009 | Sun |
| 2009/0326515 A1 | 12/2009 | Kagan |
| 2010/0021961 A1 | 1/2010 | Fujisato et al. |
| 2010/0040687 A1 | 2/2010 | Pedrozo et al. |
| 2010/0058952 A1 | 3/2010 | Yang et al. |
| 2010/0168689 A1 | 7/2010 | Swain et al. |
| 2010/0168720 A1 | 7/2010 | Swain et al. |
| 2010/0168870 A1 | 7/2010 | Swain et al. |
| 2010/0179515 A1 | 7/2010 | Swain et al. |
| 2010/0209408 A1 | 8/2010 | Stephen et al. |
| 2010/0272782 A1 | 10/2010 | Owens et al. |
| 2010/0322908 A1 | 12/2010 | Everland et al. |
| 2011/0002996 A1 | 1/2011 | McQuillan et al. |
| 2011/0020271 A1 | 1/2011 | Niklason et al. |
| 2011/0184357 A1 | 7/2011 | Robinson et al. |
| 2011/0251566 A1 | 10/2011 | Zimnitsky et al. |
| 2012/0010728 A1 | 1/2012 | Sun et al. |
| 2012/0040013 A1 | 2/2012 | Owens et al. |
| 2013/0053960 A1 | 2/2013 | Park et al. |
| 2013/0121970 A1 | 5/2013 | Owens et al. |
| 2013/0122068 A1 | 5/2013 | Fermanian et al. |
| 2013/0158676 A1 | 6/2013 | Hayzlett et al. |
| 2013/0280223 A1 | 10/2013 | Owens et al. |
| 2013/0280801 A1 | 10/2013 | Sun |
| 2015/0037436 A1 | 2/2015 | Huang et al. |
| 2015/0335686 A1 | 11/2015 | Spencer et al. |
| 2016/0166735 A1* | 6/2016 | Chang .................. A61K 38/28 424/93.7 |
| 2016/0235892 A1 | 8/2016 | Detamore et al. |
| 2016/0271295 A1 | 9/2016 | Sun et al. |
| 2017/0224869 A1 | 8/2017 | Shah et al. |
| 2018/0193520 A1 | 7/2018 | Owens |
| 2018/0193522 A1 | 7/2018 | Pomerleau et al. |
| 2018/0353644 A1 | 12/2018 | Sun et al. |
| 2019/0076582 A1 | 3/2019 | Connor |
| 2019/0111183 A1 | 4/2019 | Xu et al. |
| 2019/0117833 A1 | 4/2019 | Xu et al. |
| 2019/0262394 A1 | 8/2019 | Sun |
| 2020/0000855 A1 | 1/2020 | Xu et al. |
| 2020/0376160 A1 | 12/2020 | Xu et al. |

(56) References Cited

U.S. PATENT DOCUMENTS

| | | | |
|---|---|---|---|
| 2020/0384156 A1 | 12/2020 | Xu et al. | |
| 2021/0038767 A1 | 2/2021 | Xu et al. | |

FOREIGN PATENT DOCUMENTS

| | | | |
|---|---|---|---|
| EP | 1433423 B1 | 12/2008 | |
| WO | WO-1990/00060 A1 | 1/1990 | |
| WO | WO-1998/44809 A1 | 10/1998 | |
| WO | WO-1999/32049 A1 | 7/1999 | |
| WO | WO-1999/65470 A1 | 12/1999 | |
| WO | WO-2000/016822 A1 | 3/2000 | |
| WO | WO-2000/047114 A1 | 8/2000 | |
| WO | WO-2002/40630 A2 | 5/2002 | |
| WO | WO-2003/017826 A2 | 3/2003 | |
| WO | WO-2003/032735 A1 | 4/2003 | |
| WO | WO-2005/009134 A1 | 2/2005 | |
| WO | 2005/120597 A1 | 12/2005 | |
| WO | WO-2007/043513 A1 | 4/2007 | |
| WO | WO-2007092929 A2 * | 8/2007 | ............ A61M 37/00 |
| WO | WO-2007/134134 A2 | 11/2007 | |
| WO | WO-2008/134305 A2 | 11/2008 | |
| WO | WO-2009/009620 A2 | 1/2009 | |
| WO | WO-2010/019753 A2 | 2/2010 | |
| WO | WO-2010/078353 A2 | 7/2010 | |
| WO | WO-2011/019822 A2 | 2/2011 | |
| WO | 2011/075183 A1 | 6/2011 | |
| WO | WO-2012/142419 A1 | 10/2012 | |
| WO | WO-2012/166784 A1 | 12/2012 | |
| WO | 2014/169299 A1 | 10/2014 | |
| WO | 2016/092106 A1 | 6/2016 | |
| WO | WO-2017/029633 A1 | 2/2017 | |
| WO | 2018/118862 A1 | 6/2018 | |
| WO | 2018/218054 A2 | 11/2018 | |

OTHER PUBLICATIONS

Allman et al., Xenogeneic extracellular matrix grafts elicit a TH2-restricted immune response. Transplantation. Jun. 15, 2001;71(11):1631-40.

Argenta et al., Vacuum-assisted closure: a new method for wound control and treatment: clinical experience. Ann Plast Surg. Jun. 1997;38(6):563-76.

Aycock et al., Parastomal hernia repair with acellular dermal matrix. J Wound Ostomy Continence Nurs. Sep.-Oct. 2007;34(5):521-3.

B-Bridge International, Inc., Type 1 Collagenase Assay Kit. Catalog # AK07. www.b-bridge.com. 4 pages (2009).

Badylak et al., Endothelial cell adherence to small intestinal submucosa: an acellular bioscaffold. Biomaterials. Dec. 1999;20(23-24):2257-63.

Badylak et al., Extracellular matrix as a biological scaffold material: Structure and function. Acta Biomater. Jan. 2009;5(1):1-13.

BC BioLibrary, Sectioning of OCT Embedded Tissue. Retrieved online at: http://www.bcbiolibrary.icapture.ubc.ca/pathologists-researchers/docs/BL.LAB.GN.002.01%20Sectioning%20of%20OCT%20Embedded%20Tissue.pdf. 4 pages, (2008).

Beniker et al., The use of acellular dermal matrix as a scaffold for periosteum replacement. Orthopedics. May 2003;26(5 Suppl):s591-6.

Blackburn et al., Negative-pressure dressings as a bolster for skin grafts. Ann Plast Surg. May 1998;40(5):453-7.

Brandi et al., Treatment with vacuum-assisted closure and cryopreserved homologous de-epidermalised dermis of complex traumas to the lower limbs with loss of substance, and bones and tendons exposure. J Plast Reconstr Aesthet Surg. Dec. 2008;61(12):1507-11.

Bruder et al., The effect of implants loaded with autologous mesenchymal stem cells on the healing of canine segmental bone defects. J Bone Joint Surg Am. Jul. 1998;80(7):985-96.

Buma et al., Tissue engineering of the meniscus. Biomaterials. Apr. 2004;25(9):1523-32.

Chaplin et al., Use of an acellular dermal allograft for dural replacement: an experimental study. Neurosurgery. Aug. 1999;45(2):320-7.

Chariker et al., Effective management of incisional and cutaneous fistulae with closed suction wound drainage. Contemporary Surgery. Jun. 1989;34:59-63.

Chen et al., Acellular collagen matrix as a possible "off the shelf" biomaterial for urethral repair. Urology. Sep. 1999;54(3):407-10.

Chinn et al., Closed wound suction drainage. J Foot Surg. Jan.-Feb. 1985;24(1):76-81.

Choi et al., Decellularized extracellular matrix derived from human adipose tissue as a potential scaffold for allograft tissue engineering. J Biomed Mater Res A. Jun. 1, 2011;97(3):292-9.

Choi et al., Fabrication of porous extracellular matrix scaffolds from human adipose tissue. Tissue Eng Part C Methods. Jun. 2010;16(3):387-96.

Collins et al., Cardiac xenografts between primate species provide evidence for the importance of the alpha-galactosyl determinant in hyperacute rejection. J Immunol. May 15, 1995;154(10):5500-10.

Costantino et al., Human dural replacement with acellular dermis: clinical results and a review of the literature. Head Neck. Dec. 2000;22(8):765-71.

Dagalakis et al., Design of an artificial skin. Part III. Control of pore structure. J Biomed Mater Res. Jul. 1980;14(4):511-28.

Dattilo et al., Medical Textiles: Application of an Absorbable Barbed Bi-directional Surgical Suture. Journal of Textile and Apparel, Technology and Management. 2002 Spring;2(2):1-5.

DeFranzo et al., Vacuum-assisted closure for the treatment of abdominal wounds. Clin Plast Surg. Apr. 2006;33(2):213-24.

Dobrin et al., Elastase, collagenase, and the biaxial elastic properties of dog carotid artery. Am J Physiol. Jul. 1984;247(1 Pt 2):H124-31.

Ducksters, Chemistry for Kids, Chemical Mixtures. Retrieved online at: http://www.ducksters.com/science/chemistry/chemical_mixtures.php, 1 page, retrieved Nov. 10, 2015.

Edel, The use of a connective tissue graft for closure over an immediate implant covered with occlusive membrane. Clin Oral Implants Res. Mar. 1995;6(1):60-5.

Flack et al., An economic evaluation of VAC therapy compared with wound dressings in the treatment of diabetic foot ulcers. J Wound Care. Feb. 2008;17(2):71-8.

Fowler et al., Ridge Preservation Utilizing an Acellular Dermal Allograft and Demineralized Freeze-Dried Bone Allograft: Part II. Immediate Endosseous Impact Placement. J Periodontol. Aug. 2000;71(8):1360-1364.

Fowler et al., Root coverage with an acellular dermal allograft: a three-month case report. J Contemp Dent Pract. Aug. 15, 2000;1(3):47-59.

Galili et al., Interaction between human natural anti-alpha-galactosyl immunoglobulin G and bacteria of the human flora. Infect Immun. Jul. 1988;56(7):1730-7.

Galili et al., Man, apes, and Old World monkeys differ from other mammals in the expression of alpha-galactosyl epitopes on nucleated cells. J Biol Chem. Nov. 25, 1988;263(33):17755-62.

Galili, Interaction of the natural anti-Gal antibody with alpha-galactosyl epitopes: a major obstacle for xenotransplantation in humans. Immunol Today. Oct. 1993;14(10):480-2.

Gamba et al., Experimental abdominal wall defect repaired with acellular matrix. Pediatr Surg Int. Sep. 2002;18(5-6):327-31.

Gebhart et al., A radiographical and biomechanical study of demineralized bone matrix implanted into a bone defect of rat femurs with and without bone marrow. Acta Orthop Belg. 1991;57(2):130-43.

Griffey et al., Particulate dermal matrix as an injectable soft tissue replacement material. J Biomed Mater Res. 2001;58(1):10-5.

Hammond et al., Parastomal hernia prevention using a novel collagen implant: a randomised controlled phase 1 study. Hernia. Oct. 2008;12(5):475-81.

Ju et al., Beneficial effect of hydrophilized porous polymer scaffolds in tissue-engineered cartilage formation. J Biomed Mater Res B Appl Biomater. Apr. 2008;85(1):252-60.

Kay et al., Guided bone regeneration: integration of a resorbable membrane and a bone graft material. Pract Periodontics Aesthet Dent. Mar. 1997;9(2):185-94.

(56) References Cited

OTHER PUBLICATIONS

KCI Licensing, Inc., V.A.C.® Therapy Safety Information. 4 pages, (2007).
Kish et al., Acellular dermal matrix (AlloDerm): new material in the repair of stoma site hernias. Am Surg. Dec. 2005;71(12):1047-50.
Kridel et al., Septal perforation repair with acellular human dermal allograft. Arch Otolaryngol Head Neck Surg. Jan. 1998;124(1):73-8.
Laidlaw et al., Tympanic membrane repair with a dermal allograft. Laryngoscope. Apr. 2001;111(4 Pt 1):702-7.
Lee et al., In vitro evaluation of a poly(lactide-co-glycolide)-collagen composite scaffold for bone regeneration. Biomaterials. Jun. 2006;27(18):3466-72.
Lu et al., Novel porous aortic elastin and collagen scaffolds for tissue engineering. Biomaterials. Oct. 2004;25(22):5227-37.
Marzaro et al., Autologous satellite cell seeding improves in vivo biocompatibility of homologous muscle acellular matrix implants. Int J Mol Med. Aug. 2002;10(2):177-82.
Masters, Reliable, inexpensive and simple suction dressings. Br J Plast Surg. Apr. 1998;51(3):267.
O'Brien et al., The effect of pore size on cell adhesion in collagen-GAG scaffolds. Biomaterials. Feb. 2005;26(4):433-41.
O'Connor et al., Vacuum-assisted closure for the treatment of complex chest wounds. Ann Thorac Surg. Apr. 2005;79(4):1196-200.
Parnigotto et al., Experimental defect in rabbit urethra repaired with acellular aortic matrix. Urol Res. Jan. 2000;28(1):46-51.
Randall et al., Use of an acellular regenerative tissue matrix in combination with vacuum-assisted closure therapy for treatment of a diabetic foot wound. J Foot Ankle Surg. Sep.-Oct. 2008;47(5):430-3.
Reddy et al., Regeneration of functional bladder substitutes using large segment acellular matrix allografts in a porcine model. J Urol. Sep. 2000;164(3 Pt 2):936-41.
Simon et al., Early failure of the tissue engineered porcine heart valve SYNERGRAFT in pediatric patients. Eur J Cardiothorac Surg. Jun. 2003;23(6):1002-6.
Suckow et al., Enhanced bone regeneration using porcine small intestinal submucosa. J Invest Surg. Sep.-Oct. 1999;12(5):277-87.
Wei et al., Construction of varying porous structures in acellular bovine pericardia as a tissue-engineering extracellular matrix. Biomaterials. May 2005;26(14):1905-13.
Wu et al., An Injectable Adipose Matrix for Soft Tissue Reconstruction. Plastic and Reconstructive Surgery Advance Online Article. DOI: 10.1097/PRS.0b013e31824ec3dc. 33 pages, (2012).
Wu et al., Preparation of collagen-based materials for wound dressing. Chin Med J (Engl). Mar. 2003;116(3):419-23.
Xu et al., A porcine-derived acellular dermal scaffold that supports soft tissue regeneration: removal of terminal galactose-alpha-(1,3)-galactose and retention of matrix structure. Tissue Eng Part A. Jul. 2009;15(7):1807-19.
Yang et al., A cartilage ECM-derived 3-D porous acellular matrix scaffold for in vivo cartilage tissue engineering with PKH26-labeled chondrogenic bone marrow-derived mesenchymal stem cells. Biomaterials. May 2008;29(15):2378-87.
Zhao et al., The study of the feasibility of segmental bone defect repair with tissue-engineered bone membrane: a qualitative observation. Strategies Trauma Limb Reconstr. Sep. 2008;3(2):57-64.
Zheng et al., Porcine small intestine submucosa (SIS) is not an acellular collagenous matrix and contains porcine DNA: possible implications in human implantation. J Biomed Mater Res B Appl Biomater. Apr. 2005;73(1):61-7.
AlloDerm® Regenerative Tissue Matrix. LifeCell.com. Online product description. 1 page, Apr. 2009.
LifeCell Corporation, Alloderm Tissue Matrix defined. retrieved online at: http://www.lifecell.com/alloderm-regenerative-tissue-matrix/95. 1 page, (2009).
Liu et al., Microbial production of hyaluronic acid: current state, challenges, and perspectives. Microb Cell Fact. 2011;10:99, 9 pages.
U.S. Appl. No. 13/446,422, filed Apr. 13, 2012, U.S. Pat. No. 9,375,513, Issued.
U.S. Appl. No. 15/166,848, filed May 27, 2016, U.S. Pat. No. 10,828,391, Issued.
U.S. Appl. No. 16/108,581, filed Aug. 22, 2018, 2018-0353644, Published.
U.S. Appl. No. 13/483,674, filed May 30, 2012, 2012-0310367, Abandoned.
U.S. Appl. No. 16/189,468, filed Nov. 13, 2018, 2019-0076582, Published.
U.S. Appl. No. 13/868,588, filed Apr. 23, 2013, U.S. Pat. No. 9,782,436, Issued.
U.S. Appl. No. 15/684,402, filed Aug. 23, 2017, U.S. Pat. No. 10,314,861, Issued.
U.S. Appl. No. 16/409,120, filed May 10, 2019, 2019-0262394, Published.
U.S. Appl. No. 16/164,177, filed Oct. 18, 2018, U.S. Pat. No. 10,821,205, Issued.
U.S. Appl. No. 16/502,640, filed Jul. 3, 2019, 2020-0000855, Published.
U.S. Appl. No. 17/072,207, filed Oct. 16, 2020, 2021-0038767, Published.
U.S. Appl. No. 16/164,975, filed Oct. 19, 2018, 2019-0117833, Published.
Abu-Hakmeh et al., Sequential gelation of tyramine-substituted hyaluronic acid hydrogels enhances mechanical integrity and cell viability. Med Biol Eng Comput. Dec. 2016;54(12):1893-1902.
Busso et al., Hand augmentation with Radiesse (Calcium hydroxylapatite). Dermatol Ther. Nov.-Dec. 2007;20(6):385-7.

\* cited by examiner

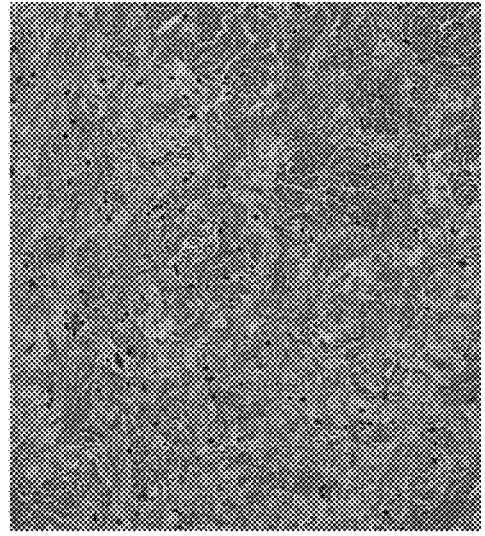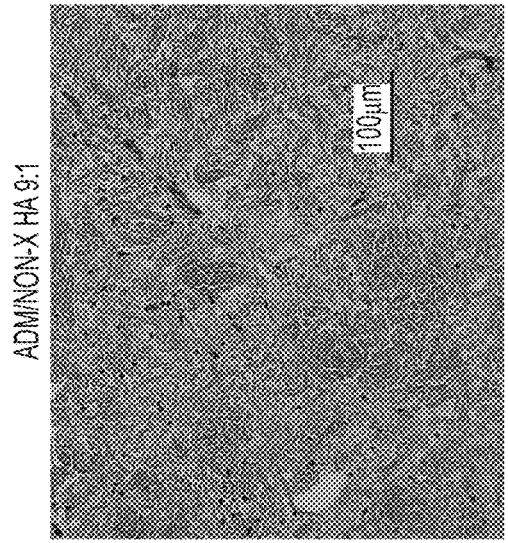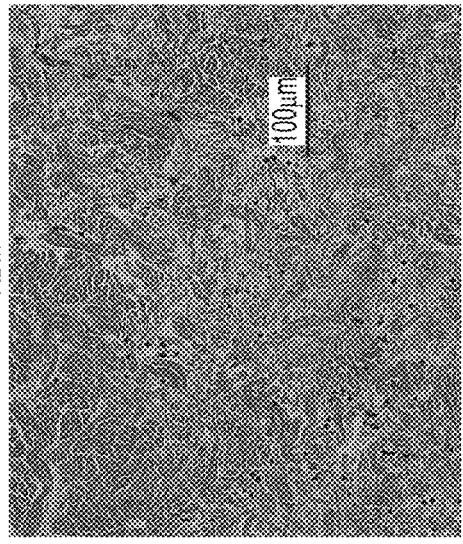

METHODS FOR INTRODUCTION OF FLOWABLE ACELLULAR TISSUE MATRIX PRODUCTS INTO A HAND

The present disclosure is a continuation-in-part of U.S. application Ser. No. 16/164,975, filed on Oct. 19, 2018, which claims priority under 35 USC § 119 to U.S. Provisional Application 62/574,678, which was filed on Oct. 19, 2017 and is herein incorporated by reference.

The present disclosure relates to the introduction of tissue matrices to a patient, and more particularly to the hand of a patient, for surgical or medical procedures including tissue regeneration for aesthetic or non-aesthetic purposes.

There is currently a need for improved injectable materials for tissue treatment. For example, to treat various conditions exhibited in a hand (e.g., wasting, wrinkles, insufficient volume, or less than desirable shapes or forms), injectable materials such as hyaluronic-acid-based materials may be used. Such materials, however effective, may provide only temporary improvements due to eventual resorption by the body. Although work has been done to develop hyaluronic acid (HA) materials that last longer in vivo before resorption by, for example, cross-linking the HA, the current materials will still inevitably be resorbed by the body following injection.

There exists an unmet need for tissue product compositions that can produce longer lasting effects while being suitable for injection through a syringe or otherwise easily handled injection device or implantation system.

Accordingly, the present disclosure provides methods of delivering tissue product compositions having acellular tissue matrix particles mixed within a flowable carrier comprising a hyaluronic acid based material. In addition, methods of treatment using such compositions are provided.

The present disclosure provides methods of treatment using the disclosed tissue product compositions. The methods include identifying at least one area of a hand to be treated, inserting a tip of a needle or cannula fluidly coupled to a reservoir defining a volume into the at least one area, the reservoir holding a tissue product composition, and injecting the composition between a dermal layer and a fascia layer of the at least one area. The tissue composition includes a flowable carrier comprising a hyaluronic acid based material and a plurality of acellular tissue matrix particles mixed within the carrier.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

FIGS. 17A-D is a group of microscope photographs comparing biological responses observed for implanted tissue product compositions with and without a flowable hyaluronic acid carrier;

DETAILED DESCRIPTION OF CERTAIN EXEMPLARY EMBODIMENTS

Figure 1:
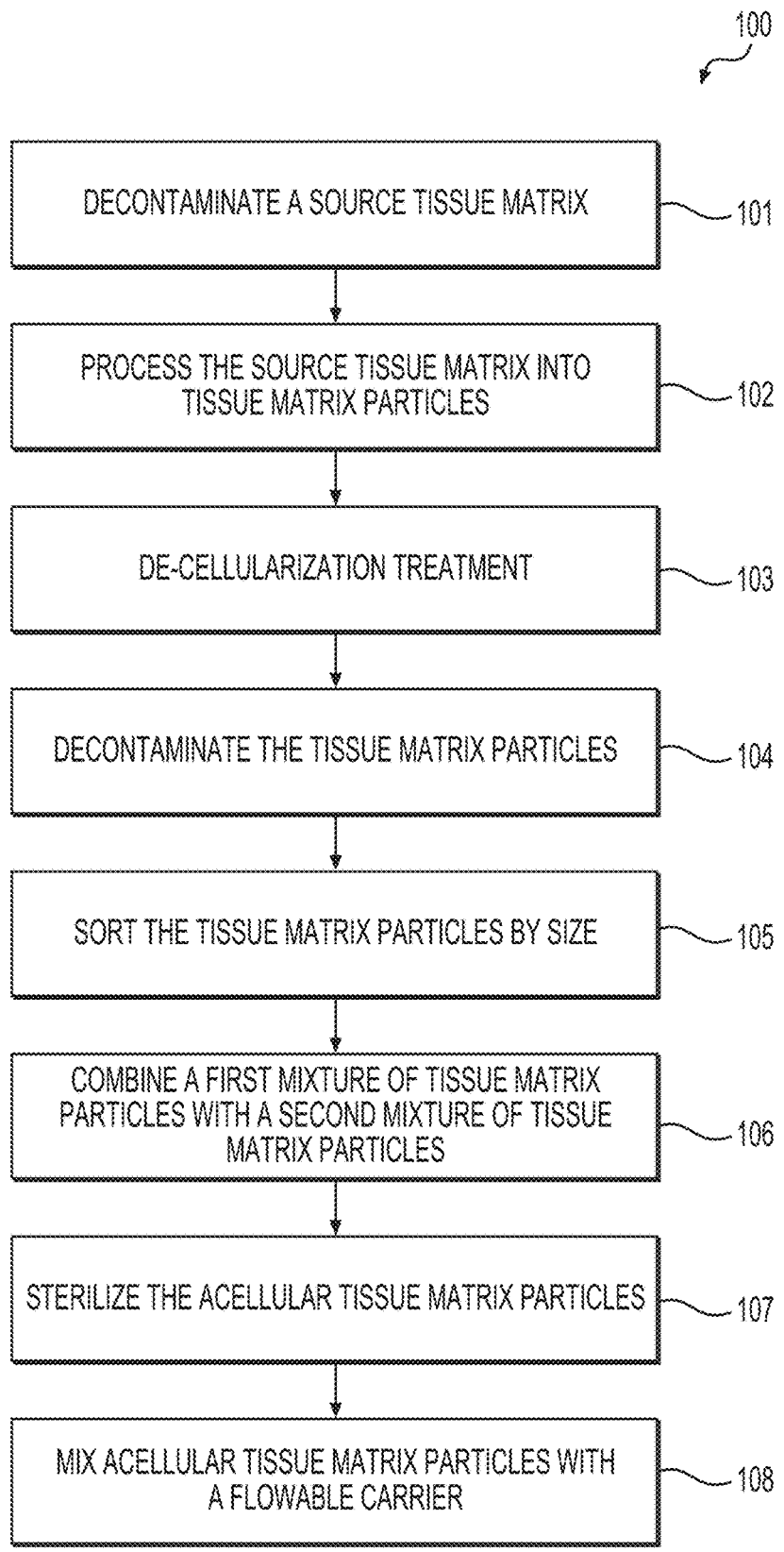
FIG. 1 is a flow chart illustrating an exemplary embodiment of a method for producing tissue products provided in accordance with the present invention.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Similarly, the use of the term "comprising," as well as other forms, such as "comprises," is also not limiting. Any range described herein will be understood to include the endpoints and all values between the endpoints.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

As used herein, the term "acellular tissue matrix" refers to an extracellular matrix derived from human or animal tissue, wherein the matrix retains a substantial amount of natural collagen and glycoproteins needed to serve as a scaffold to support tissue regeneration. "Acellular tissue matrices" are different from purified collagen materials, such as acid-extracted purified collagen, which are substantially void of other matrix proteins and do not retain the natural microstructural features of tissue matrix due to the purification processes. Although referred to as "acellular tissue matrices," it will be appreciated that such tissue matrices may combine with exogenous cells, including, for example, stem cells, or cells from a patient in whom the "acellular tissue matrices" may be implanted. Further, it should be appreciated that "acellular tissue matrix particles" refers to particulate of an acellular tissue matrix, as will be described further herein.

"Acellular" or "decellularized" tissue matrices will be understood to refer to tissue matrices in which no cells are visible using light microscopy.

Various human and animal tissues may be used to produce products for treating patients. For example, various tissue products for regeneration, repair, augmentation, reinforcement, and/or treatment of human tissues that have been damaged or lost due to various diseases and/or structural damage (e.g., from trauma, surgery, atrophy, and/or long-term wear and degeneration) have been produced. Such products may include, for example, acellular tissue matrices, tissue allografts or xenografts, and/or reconstituted tissues (i.e., at least partially decellularized tissues that have been seeded with cells to produce viable materials).

The tissue products may include acellular tissue matrix particles from dermal or other tissues that have been processed to remove at least some of the cellular components. In some cases, all, or substantially all, cellular materials are removed, thereby leaving corresponding extracellular matrix proteins. While dermal tissue is primarily described herein as being the source tissue for exemplary embodiments of acellular tissue matrix particles, it should be appreciated that the acellular tissue matrix particles described herein can originate from other tissue types. Other exemplary tissue types include, but are not limited to: adipose tissue, small intestine submucosa (SIS) tissue, muscle tissue, vascular tissue, and bone tissue.

The source tissues described herein may be derived from human or animal sources. For example, tissue may be obtained from cadavers. In addition, human tissue could be obtained from live donors (e.g., autologous tissue). Tissue may also be obtained from animals such as pigs, monkeys, or other sources. If animal sources are used, the tissues may be further treated to remove antigenic components such as 1,3-alpha-galactose moieties, which are present in pigs and other mammals, but not humans or primates. In addition, the tissue may be obtained from animals that have been genetically modified to remove antigenic moieties. See Xu, Hui. et al., "A Porcine-Derived Acellular Dermal Scaffold that Supports Soft Tissue Regeneration: Removal of Terminal Galactose-α-(1,3)-Galactose and Retention of Matrix Structure," Tissue Engineering, Vol. 15, 1-13 (2009), which is hereby incorporated by reference in its entirety.

As used herein, a "hyaluronic acid based material" is a material comprising hyaluronic acid (HA). HA refers to hyaluronic acid and can also refer to any salts thereof, including, but not limited to, sodium hyaluronate, potassium hyaluronate, magnesium hyaluronate, calcium hyaluronate, and combinations thereof. Both HA and pharmaceutically acceptable salts thereof can be included in the hyaluronic acid based material. Exemplary HA based materials are commercially sold as JUVEDERM® and JUVEDERM VOLUMA®. It should be appreciated that the hyaluronic acid based material may include additional agents such as, for example, lidocaine.

All numbers herein expressing "molecular weight" of HA are to be understood as indicating the weight average molecular weight (Mw) in Daltons.

The molecular weight of HA is calculated from an intrinsic viscosity measurement using the following Mark Houwink relation: Intrinsic Viscosity (m3/kg)=$9.78 \times 10^{-5} \times Mw^{0.690}$. The intrinsic viscosity is measured according to the procedure defined European Pharmacopoeia (HA monograph No 1472, January 2009).

High molecular weight HA as used herein describes a HA material having a molecular weight of at least about 1.0 million Daltons (mw≥$10^6$ Da or 1 MDa) to about 4.0 MDa. High molecular weight HA that may be incorporated in the present tissue product compositions may have a molecular weight in the range about 1.5 MDa to about 3.0 MDa, or the high molecular weight HA may have a weight average molecular weight of about 2.0 MDa. In another example, the high molecular weight HA may have a molecular weight of about 3.0 MDa.

Low molecular weight HA as used herein describes a HA material having a molecular weight of less than about 1.0 MDa. Low molecular weight HA can have a molecular weight of between about 200,000 Da (0.2 MDa) to less than 1.0 MDa, for example, between about 300,000 Da (0.3 M Da) to about 750,000 Da. (0.75 MDa), up to but not exceeding 0.99 MDa. Preferably, there is no overlap between the molecular weight distribution of the low and high molecular weight HA materials. Preferably, the mixture of the low molecular weight HA and high molecular weight HA has a bimodal molecular weight distribution. The mixture may also have a multi-modal distribution.

In one aspect of the invention, the tissue product compositions comprise HA having a high molecular weight component and a low molecular weight component, and the high molecular weight component may have a weight average molecular weight at least twice the weight average molecular weight of the low molecular weight component. For example, the molecular weight ratio of the high molecular weight HA to the low molecular weight HA in the composition may be at least 2:1. For example, a tissue product composition may include an HA having a low molecular weight component having a weight average molecular weight of about 500,000 Da, and a high molecular weight component having a weight average molecular weight of about, or at least about, 1.0 MDa. In another example, a tissue product composition in accordance with the invention may include an HA having a low molecular weight component having a weight average molecular weight of about 800,000 Da, and a high molecular weight component having a weight average molecular weight of about, or at least about, 1.6 MDa. It should be appreciated that many different types of HA may be incorporated in the tissue product composition, and the foregoing examples are not intended to be limiting.

In some exemplary embodiments, the HA may be cross-linked using one or more suitable crosslinking agents. The crosslinking agent may be any agent known to be suitable for crosslinking polysaccharides and their derivatives via their hydroxyl groups. Suitable crosslinking agents include but are not limited to, 1,4-butanediol diglycidyl ether (or 1,4-bis(2,3-epoxypropoxy)butane or 1,4-bisglycidyloxybutane, all of which are commonly known as BDDE), 1,2-bis (2,3-epoxypropoxy)ethylene, 1-(2,3-epoxypropyl)-2,3-epoxycyclohexane, and 1-ethyl-3-(3-dimethylaminopropyl) carbodiimide hydrochloride (commonly known as EDC). Other suitable hyaluronan crosslinking agents include multifunctional PEG-based crosslinking agents like pentaerythritol tetraglycidyl ether (PETGE), divinyl sulfone (DVS), 1,2-bis(2,3-epoxypropoxy)ethylene (EGDGE), 1,2,7,8-diepoxyoctane (DEO), (phenylenebis-(ethyl)-carbodiimide and 1,6 hexamethylenebis (ethylcarbodiimide), adipic dihydrazide (ADH), bis(sulfosuccinimidyl)suberate (BS), hexamethylenediamine (HMDA), 1-(2,3-epoxypropyl)-2,3-epoxycyclohexane, or combinations thereof.

In one exemplary embodiment of a tissue product composition formed in accordance with the present invention, the tissue product composition includes a flowable carrier comprising a hyaluronic acid based material and a plurality of acellular tissue matrix particles mixed within the carrier. In some exemplary embodiments, the flowable carrier comprises HA that has not been mixed with additional agents; in other exemplary embodiments, the flowable carrier comprises HA mixed with additional agents. Additional agents may include, but are not limited to, anesthetic agents for example, aminoamide local anesthetic and salts thereof or an aminoester local anesthetic and salts thereof. For example, procaine, chloroprocaine, cocaine, cyclomethycaine, cimethocaine, propoxycaine, procaine, proparacaine, tetracaine, or salts thereof, or any combination thereof. In some embodiments, anesthetic agents may comprise articaine, bupivacaine, cinchocaine, etidocaine, levobupivacaine, lidocaine, mepivacaine, piperocaine, prilocaine, ropivacaine, trimecaine, or salts thereof, or any combination thereof.

The flowable carrier may initially be in the form of a flowable liquid solution that can be mixed with the tissue matrix particles to form a slurry. The formed slurry can then be loaded into a syringe or other injection device for administration to a patient. In some exemplary embodiments, the flowable carrier may be a non-crosslinked HA in an amount sufficient to provide improved injectability of the tissue product composition. While the flowable carrier is described herein as comprising HA, it is contemplated that other glycosaminoglycans (GAGs) may be utilized as the flowable carrier, such as HSGAG, CSGAG, and/or keratin sulfate type GAGs.

The acellular tissue matrix particles may originate from a human or animal tissue matrix, as previously described. Suitable tissue sources may include allograft, autograft, or xenograft tissues. When xenografts are used, the tissue may include tissues from animals including porcine, cow, dog, cat, domestic or wild sources, and/or any other suitable mammalian or non-mammalian tissue source. In some exemplary embodiments, the acellular tissue matrix particles may originate from a source dermal matrix taken from an animal, such as a pig. In one exemplary embodiment, the source dermal matrix may comprise one or more layers of skin that have been removed from an organism. The size and shape of the source tissue matrix may be varied, according to known methods, to produce differing amounts of acellular tissue matrix particles, as will be described further herein.

The source tissue may be harvested from animal sources using any desirable technique, but may be generally obtained using, if possible, aseptic or sterile techniques. The tissue may be stored in cold or frozen conditions or may be immediately processed to prevent any undesirable changes due to prolonged storage.

Acellular tissue matrices can provide a suitable tissue scaffold to allow cell ingrowth and tissue regeneration. In the context of skin lines, wrinkles, etc., a tissue scaffold could represent a long-term solution to filling in lost volume without needing to be replaced like HA or other temporary filler materials. The tissue scaffolds can be injected into existing or damaged skin to allow production of a thicker dermis at the injection site. Tissue scaffolds may also be useful in other medical applications, such as large volume tissue repair.

One particular problem that has been identified with using an acellular tissue matrix is the difficulty of placement, such as injecting, acellular tissue matrix material in its natural form, due to the network formed by the tissue matrix. While surgical implantation is a suitable option for implanting acellular tissue matrix materials to repair certain areas of the body, injection may be preferred for some applications, including for treatment of a hand. Particulating the acellular tissue matrix was found to be an improvement for application and injection, compared to applying the acellular tissue matrix in its natural form, but it was found that even particulated pure acellular tissue matrix was not easily applied or injected into a patient. Particularly, application of the particulated tissue matrix material was found to be difficult to control. Further, the injection force required to inject particulated acellular tissue matrix was found to be relatively high, and it was found to be relatively difficult to inject all of the particulated tissue matrix loaded into an injection device, such as a syringe.

To address some of the previously described problems of injecting acellular tissue matrix materials, exemplary embodiments described herein provide tissue product compositions including acellular tissue matrix particles mixed within a flowable carrier comprising a hyaluronic acid based material. The formed tissue product composition can be more easily applied than pure acellular tissue matrix particles, as will be described further herein, while maintaining characteristics that encourage tissue growth in the implantation and/or injection area. The formed tissue product also provides improved spreadability in the hand.

The tissue product compositions described herein may be used to treat a variety of different anatomic sites. In one exemplary embodiment, the tissue product compositions may be formed as an injectable tissue product composition suitable for small-volume implantations, e.g., to treat lines, wrinkles, voids, or divots, to add volume (e.g., by increasing dermal thickness), or replace small volumes of lost tissue. In other exemplary embodiments, the tissue product compositions may be formed as a putty or paste suitable for larger volume implantations such as repairing large areas of structural tissue, breast tissue replacement, or any other area where a relatively large volume of damaged and/or lost tissue must be repaired and/or replaced. In other exemplary embodiments, the tissue product compositions may be formed as an injectable tissue product composition suitable for use in applications where HA or other fillers would be utilized, with the injected tissue product composition representing a long-term, rather than short-term, treatment. In other exemplary embodiments, the tissue product compositions are suitable for treatment of wasting in a hand. In yet other exemplary embodiments, the tissue product compositions may be originated from more than one sources. For example, a tissue product composition can be originated from a dermal matrix and an adipose matrix.

Referring now to FIG. 1, an exemplary embodiment of a method 100 for producing a tissue product composition in accordance with the present invention is illustrated. The method 100 generally includes mixing a plurality of acellular tissue matrix particles within a flowable carrier comprising a hyaluronic acid based material to produce the tissue product composition. In some exemplary embodiments, the method 100 may also include processing 102 a source tissue matrix, such as a source dermal matrix, to produce the acellular tissue matrix particles prior to mixing 108 the acellular tissue matrix particles with the flowable carrier. In one exemplary embodiment, the method 100 includes initially decontaminating 101 the source tissue matrix to remove contaminants, such as dirt or other debris or microbes, to clean and prepare the source tissue matrix for processing 102. In some exemplary embodiments, the decontaminating 101 may comprise washing the source tissue matrix. For example, the source tissue matrix may be washed with one or more rinses with various biocompatible buffers. For example, suitable wash solutions may include saline, phosphate buffered saline, or other suitable biocompatible materials or physiological solutions. In one exemplary embodiment, water may be used as a rinsing agent to further break the cells, after which phosphate buffered saline, or any other suitable saline solution, may be introduced to allow the matrix proteins to return to biocompatible buffers. A large variety of other suitable decontamination processes are known, so further description of the decontamination is omitted for brevity.

The source tissue matrix is processed 102 to break up the source tissue matrix into a plurality of tissue matrix particles. The source tissue matrix may, generally speaking, be in a form that is initially unsuitable for easy application or injection through a syringe or other injection device, due to the structure of the source tissue matrix. For example, a source dermal matrix may be in the form of a planar sheet, which is not easily worked with or loaded into or expelled from an injection device. To process 102 the source tissue matrix, a grinder or other mechanical separation device may be employed to break up the source tissue matrix into tissue matrix particles by grinding, blending, chopping, grating, and/or other mechanical agitation of the source tissue matrix. In some exemplary embodiments, the processing 102 may produce tissue matrix particles having many different particle sizes (diameters), which will be described further herein.

In some cases, the processing 102 may be performed by mechanically processing the tissue with the addition of little or no washing or lubricating fluids. For example, the tissue may be mechanically processed by grinding or blending without the use of solvents. When grinding the tissue requires moisture, for example, water may be used over other solutions, such as saline or phosphate buffered saline. Alternatively, the tissue may be processed by adding a certain quantity of solvent that is biocompatible, such as saline (e.g., normal saline, phosphate buffered saline, or solutions including salts and/or detergents). Other solutions that facilitate cell lysis may also be appropriate.

The method 100 may further include de-cellularizing 103 the source tissue matrix or produced tissue matrix particles to remove substantially all of the native cellular material, which may cause an antigenic response in the patient following injection. The de-cellularization 103 may include a number of suitable processes. For example, suitable methods for removing cells from the source tissue matrix or tissue matrix particles may include treatment with detergents such as deoxycholic acid, polyethylene glycols, or other detergents at concentrations and times sufficient to disrupt cells and/or remove cellular components. In some exemplary embodiments, the the de-cellularization 103 may occur after processing 102 the source tissue matrix into tissue matrix particles; in other exemplary embodiments, the de-cellularization 103 may occur prior to processing 102 the source tissue matrix into tissue matrix particles. In still other exemplary embodiments, de-cellularization 103 may take place both before and after processing 102 the source tissue matrix into tissue matrix particles. Regardless of when de-cellularization 103 takes place, acellular tissue matrix particles should be produced following both the processing 102 and de-cellularization 103.

Optionally, the method 100 may include additionally decontaminating 104 the formed acellular tissue matrix particles to remove contaminants that may have been inadvertently introduced or produced during the processing 102 and/or de-cellularization 103. The decontamination 104 may be similar to the previously described decontamination 101, or may comprise additional washing or treatment of the acellular tissue matrix particles. For example, additional washing or treatment may be performed to remove antigenic materials such as alpha-1,3-galactose moieties, which may be present on non-primate animal tissues. In addition, during, before, and/or after the washing steps, additional solutions or reagents may be used to process the material. For example, enzymes, detergents, and/or other agents may be used in one or more steps to further remove cellular materials or lipids, remove antigenic materials, and/or reduce the bacteria or other bioburden of the material. For example, one or more washing steps may be included using detergents, such as sodium dodecylsulfate or TRIS to assist in cell and lipid removal. In addition, enzymes such as lipases, DNAses, RNAses, alpha-galactosidase, or other enzymes may be used to ensure destruction of nuclear materials, antigens from xenogenic sources, residual cellular components and/or viruses. Further, acidic solutions and/or peroxides may be used to help further remove cellular materials and destroy bacteria and/or viruses, or other potentially infectious agents.

In some exemplary embodiments, the acellular tissue matrix particles may be sterilized 107 prior to or after mixing 108 with the flowable carrier. In one exemplary embodiment, the sterilization 107 may comprise electron-beam sterilization, as is known in the art. Alternative sterilization techniques may also be employed, as is known in the art.

The acellular tissue matrix particles and flowable carrier can be mixed 108 in any suitable way. In one exemplary embodiment, the acellular tissue matrix particles and flowable carrier may be mixed in a large volume batch under generally sterile conditions to form a tissue product composition in accordance with the present invention. The mixing 108 may comprise, for example, stirring the acellular tissue matrix particles and flowable carrier together to form a slurry. The parameters and technique of the mixing 108 may be altered according to the properties of the flowable carrier and the acellular tissue matrix particles, as well as the general amounts of each in the tissue product composition, and can be readily derived by one skilled in the art from routine experimentation.

In some exemplary embodiments, the hyaluronic acid based material is cross-linked for stabilization. The cross-linking may occur before, after, or during mixing 108 with the acellular tissue matrix particles. In some exemplary embodiments, the material is cross-linked after freeze drying. However, the material can also be cross-linked before or during the freeze-drying process. Cross-linking may be performed in a variety of ways. In one exemplary embodiment, cross-linking occurs by contacting the hyaluronic acid based material with one or more cross-linking agents such as glutaraldehyde, genepin, carbodiimides (e.g., 1-ethyl-3-(3-dimethylaminopropyl) carbodiimide hydrochloride (EDC)), diisocyantes, or 1,4-butanediol diglycidyl ether (or 1,4-bis(2,3-epoxypropoxy)butane or 1,4-bisglycidyloxybutane, all of which are commonly known as BDDE. In addition, cross-linking may be performed by heating the material. For example, in some embodiments, the material may be heated to between 70° C. to 120° C., or between 80° C. and 110° C., or to about 100° C., or any values between the specified ranges in a reduced pressure or vacuum. In addition, other cross-linking processes, or combination of processes may be used to produce any of the disclosed cross-linked products, including ultraviolet irradiation, gamma irradiation, and/or electron beam irradiation. In addition, a vacuum is not needed but may reduce cross-linking time. Further, lower or higher temperatures could be used as long as melting of the matrix proteins does not occur and/or sufficient time is provided for cross-linking.

In various embodiments, the cross-linking process may be controlled to produce a tissue product composition with desired mechanical, biological, and/or structural features. For example, cross-linking may influence the overall strength of the tissue product composition, and the process may be controlled to produce a desired strength. In addition, the amount of cross-linking may affect the ability of the tissue product composition to maintain a desired shape and structure (e.g., porosity) when implanted. Accordingly, the amount of cross-linking may be selected to produce a stable three-dimensional shape when implanted in a body, when contacted with an aqueous environment, and/or when compressed (e.g., by surrounding tissues or materials).

Excessive cross-linking may change the extracellular matrix materials. For example, excessive cross-linking may damage collagen or other extracellular matrix proteins. The damaged proteins may not support tissue regeneration when the tissue product compositions are injected in a patient. In addition, excessive cross-linking may cause the material to be brittle or weak. Accordingly, the amount of cross-linking may be controlled to produce a desired level of stability, while maintaining desired biological, mechanical, and/or structural features.

In some exemplary embodiments, seed cells may be introduced into the flowable carrier and/or acellular tissue matrix particles before, during, or after mixing 108. The seed cells may, in some embodiments, comprise cells from a patient, i.e., autologous cells, for seeding into the tissue product composition prior to application of the tissue product composition. In some exemplary embodiments, the seed cells may be cultured with the flowable carrier and acellular tissue matrix particles prior to application; in other exemplary embodiments, the seed cells may be applied to the tissue product composition following application. The seed cells may include, but are not limited to, adipocytes, various stem cells, blood cells, etc., which may promote adhesion, infiltration, and/or growth of other cells to the injected tissue product composition. Similarly, various growth factors or other substances can be included in the tissue product composition to encourage growth of cells to the injected tissue product composition.

As described previously, the tissue product compositions should have the ability to support cell ingrowth and tissue regeneration when implanted in or on a patient. In addition, the tissue product compositions may have the ability to act as a carrier for and support the growth of cells, such as autologous cells from the patient. Accordingly, the processes described herein should not alter the extracellular matrix proteins (e.g., by damaging protein structure and/or removing important glycosaminoglycans and/or growth factors). In some embodiments, the products will have normal collagen banding as evidenced by microscopy and described further herein.

In various embodiments, the tissue products are treated with a process that retains either or both of the native hyaluronic acid and chondroitin sulfate. Accordingly, the tissue products may include either or both of hyaluronic acid and chondroitin sulfate. In addition, the process may be selected to maintain native growth factors. For example, the tissue products may be produced such that the tissue products contains one or more growth factors selected from PECAM-1, HGF, VEGF, PDGF-BB, follistatin, IL-8, and FGF-basic.

A. Exemplary Tissue Product Compositions

Various hyaluronic acid based materials may be mixed with acellular tissue matrix particles to produce various tissue product compositions described in Table 1 below, in accordance with the present invention. It should be appreciated that the hyaluronic acid based materials described herein are exemplary only, and other hyaluronic acid based materials may be mixed with the acellular tissue matrix particles. Further, the compositions given in Table 1 are exemplary only, and other formulations of tissue product compositions may be formed in accordance with the present invention.

Figure 4:
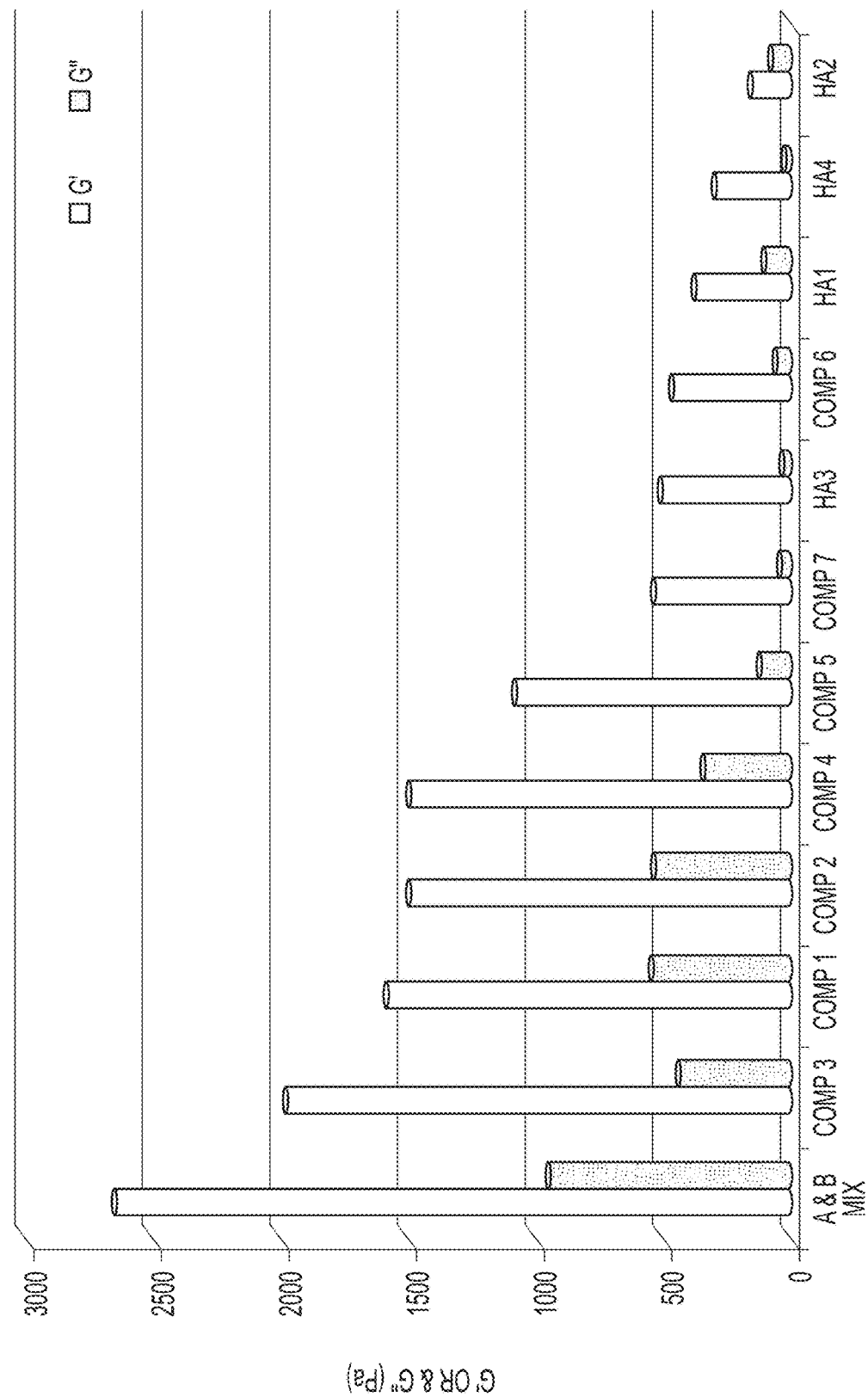
FIG. 4 is a graph illustrating G' and G" values at 5 Hz for various tissue product compositions.

To formulate the tissue product compositions described in Table 1, four different types of hyaluronic acid based materials were used. All HA Types used to form Compositions 1-11 were initially in a solution having a concentration of 20 mg HA/mL. HA Type 1 is a non-crosslinked hyaluronic acid having a G' value of 320 Pa; HA Type 2 and HA Type 3, in contrast, are hyaluronic acids that were cross-linked with an EDC cross-linking agent with different G' and G" values, as can be seen in FIG. 4, depending on the degree of cross-linking. HA Type 2 had a G' value of 160 Pa and HA Type 3 had a G' value of between 500-550. HA Type 4 is also cross-linked, but uses BDDE as the cross-linking agent. HA Type 4 may have a G' value of 350 Pa.

TABLE 1

| Composition | ADM Slurry | ADM:HA Ratio | HA Type (20 mg/mL) | [HA] (mg/mL) | [ADM] (mg/mL) |
|---|---|---|---|---|---|
| 1 | ADMS | 9:1 | HA1 | 2 | 135 |
| 2 | ADMS | 9:1 | HA2 | 2 | 135 |
| 3 | ADMS | 7:3 | HA3 | 6 | 105 |
| 4 | ADMS | 7:3 | HA4 | 6 | 105 |

TABLE 1-continued

| Composition | ADM Slurry | ADM:HA Ratio | HA Type (20 mg/mL) | [HA] (mg/mL) | [ADM] (mg/mL) |
|---|---|---|---|---|---|
| 5 | ADMS | 4:6 | HA3 | 12 | 60 |
| 6 | ADMS | 4:6 | HA4 | 12 | 60 |
| 7 | ADMS | 1:9 | HA3 | 18 | 15 |
| 8 | ADMS | 5:5 | HA1 | 10 | 75 |
| 9 | ADMS | 5:5 | HA2 | 10 | 75 |
| 10 | ADMS | 5:5 | HA2 | 10 | 75 |
| 11 | ADMS | 19:1 | HA1 | 1 | 142.5 |

Turning now to Table 1, exemplary embodiments of tissue product compositions formed in accordance with the present invention are described. Compositions 1-11, representing various tissue product compositions are illustrated in Table 1, but it should be appreciated that other tissue product compositions may be formed in accordance with the present invention. For each Composition 1-11, the acellular tissue matrix particles originated from porcine acellular dermal matrix (ADM) and, when combined with the flowable carrier, produced acellular dermal matrix slurries (ADMS), which may also be referred to as "flowable ADM." Prior to mixing with the flowable carrier, which was provided in a concentration of 20 mg HA/mL, the acellular tissue matrix particles were in a concentration of 150 mg/mL. As should be appreciated from Table 1, a ratio of ADM:HA can be adjusted to produce slurries with varying flow properties, as will be described further herein. It should be understood that the ratios described herein can be either by volume or by mass; in the exemplary embodiments shown in Table 1, the ratio is given as volume ADM:volume HA. In some exemplary embodiments, the ratio of ADM:HA can vary from between 1:9 and 19:1. As exemplified by Compositions 1 and 2, the ratio of ADM:HA can be 9:1; as exemplified by Compositions 3 and 4, the ratio of ADM:HA can be 7:3; as exemplified by Compositions 5 and 6, the ratio of ADM:HA can be 4:6; as exemplified by Composition 7, the ratio of ADM:HA can be 1:9; as exemplified by Compositions 8, 9, and 10, the ratio of ADM:HA can be 5:5; and as exemplified by Composition 11, the ratio of ADM:HA can be 19:1. It should be appreciated that the previously described ratios are exemplary only, and other exemplary embodiments of tissue product compositions may have other ratios of ADM:HA, including values between the exemplary ratios.

According to certain aspects of this disclosure, a tissue product composition with a desired tissue matrix particle solid content may be used. For example, a material that is 2% to 20% solid content, such as 10% to 15% solid content, may be desired depending on what type of hyaluronic acid based material is mixed with the tissue matrix particles. In some exemplary embodiments, the tissue product composition has 15% solid content, corresponding to 150 mg/mL, of acellular tissue matrix particles.

Referring again to FIG. 1, the method 100 of forming tissue product compositions may further include sorting 105 the tissue matrix particles by particle size. In some exemplary embodiments, the sorting 105 may include straining the tissue matrix particles through one or more sieves. While the sorting 105 is shown as occurring after de-cellularization 103 and prior to sterilization 107, it should be appreciated that the sorting 105 may occur before de-cellularization 103 and/or after sterilization 107, if desired. Further, the tissue matrix particles may be sorted in ways other than straining.

In one exemplary embodiment, the tissue matrix particles may be strained through a first sieve defining a first sieve diameter and a second sieve defining a second sieve diameter that is less than the first sieve diameter. The first sieve allows tissue matrix particles with particle sizes less than the first sieve diameter to pass through, while the second sieve allows tissue matrix particles with particle sizes less than the second sieve diameter to pass through. In this sense, a first mixture of sorted tissue matrix particles left in the first sieve can define a first average particle size greater than the first sieve diameter, and a second mixture of sorted tissue matrix particles left in the second sieve can define a second average particle size less than the first sieve diameter but greater than the second sieve diameter.

The first mixture of sorted tissue matrix particles and the second mixture of sorted tissue matrix particles may be combined 106 to produce a tissue matrix particle mixture with a desired size distribution. It should be appreciated that more than two sieves each defining a respective sieve diameter can be used to sort 105 the tissue matrix particles by particle size. In one exemplary embodiment, tissue matrix particle sizes may range from 50 microns to 3,500 microns. For example, the tissue matrix particles may be sieved to retrieve particles with the following dimensions: Extra fine particles (e.g., 50-100 microns); Fine particles (e.g., 100-400 microns); Medium particles (e.g., 0.4 mm to 0.6 mm); Large particles (e.g., 0.8 mm to 1 mm); and Larger particles (e.g., >1 mm). In some aspects of the present disclosure, particle sizes in this range may not invoke a varied biological response. In other words, for example, there may be no difference in biological responses with particle sizes ranging from 50 microns to 3,500 microns. Different applications that may require a specific size of an injection needle may select a specific size of particle(s) without the need to consider if the biological responses will be different.

Figure 2:
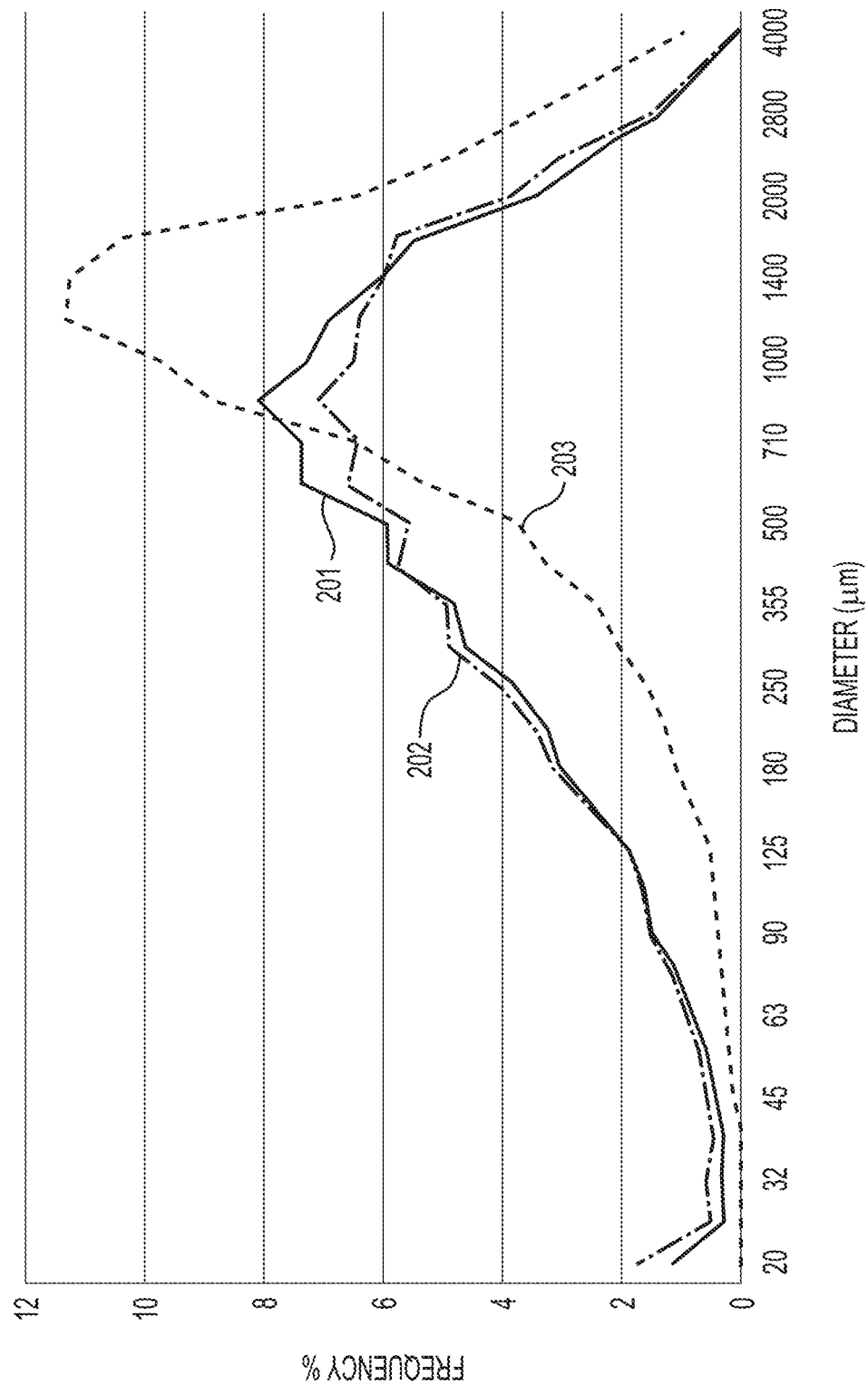
FIG. 2 is a graph illustrating exemplary embodiments of tissue product compositions having different particle size distributions.

Referring now to FIG. 2, exemplary tissue matrix particle size distributions are illustrated. As can be seen, the graph illustrates a first particle size plot 201, a second particle size plot 202, and a third particle size plot 203 of various tissue product compositions formed in the accordance with the present invention. The first particle size plot 201 shows a first tissue product composition having a majority of particle sizes ranging from 200 to 2000 μm; the second particle size plot 202 shows a second issue product composition having a majority of particle sizes ranging from 200 to 2000 μm; and the third particle size plot 203 shows a third tissue product composition having a majority of particle sizes ranging from 500 to 2500 μm, as shown. Controlling the tissue matrix particle size distribution can allow adjustment of flow and/or spread properties of the tissue product composition.

B. Properties of Exemplary Tissue Product Compositions

To determine how the properties of tissue product compositions formed in accordance with the present invention compared to pure acellular tissue matrix sheets and/or particles, various tests were conducted to measure properties of the tissue product compositions. One such test that was performed was differential scanning calorimetry (DSC) to determine the onset temperature of various exemplary embodiments of tissue product compositions including a flowable carrier comprising a hyaluronic acid based material and acellular tissue matrix particles. From DSC analysis, it was found that the tested tissue product compositions with the flowable carrier and acellular tissue matrix particles can have an onset temperature in a range between 55° C. and 60° C., which is similar to the onset temperature (56° C.-58° C.) of sheet acellular dermal matrix.

Figure 3:
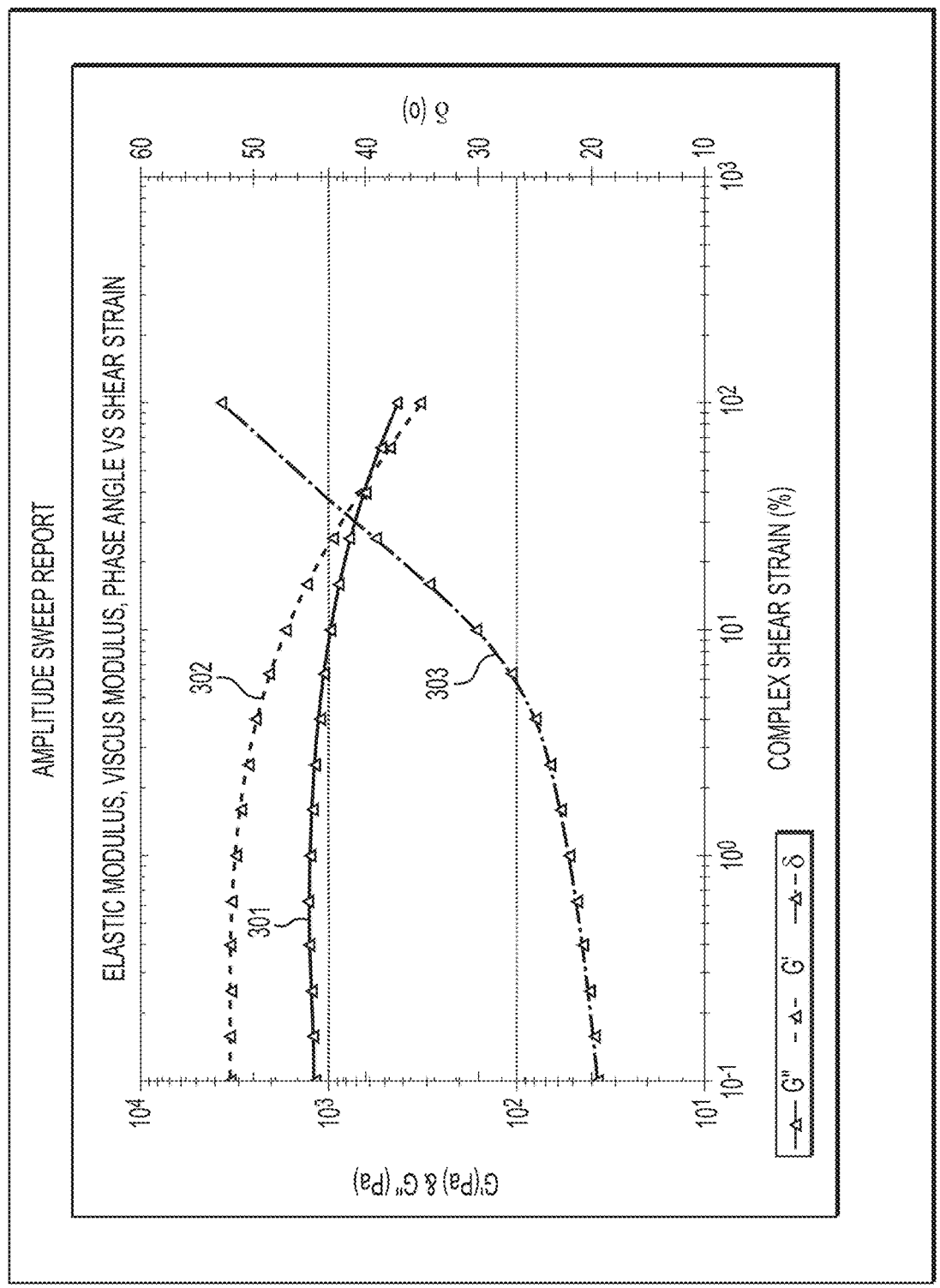
FIG. 3 is a graph illustrating an amplitude sweep report for a tissue product composition comprising acellular tissue matrix particles that are not mixed within a flowable carrier.

Referring now to FIGS. 3 and 4, rheology analyses of various tissue product compositions are illustrated. FIG. 3 illustrates an amplitude sweep report of acellular dermal matrix in a flowable (slurry) form having 15% solid content, corresponding to a concentration of 150 mg/mL. The frequency sweep used was 0.3% strain to determine an elastic ("storage") modulus (G') plot 301, a viscous ("loss") modulus (G") plot 302, and a phase angle (δ) plot 303 as functions of complex sheer strain percentages. As is known in rheology, G' generally indicates the ability of a material to recover its shape after deformation, i.e., elasticity, while G" generally indicates the viscosity of a material.

Referring now to FIG. 4, G' and G" values of various tissue product compositions and flowable carriers are illustrated. The G' and G" values in FIG. 4 were determined using amplitude sweep at a frequency of 5 Hz; the G' value is shown on the left for each material, while the G" value is shown on the right for each material. As can be seen, the G' and G" values for pure tissue matrix are higher than respective values of any one of Compositions 1-7 including tissue matrix particles mixed within a flowable carrier comprising a hyaluronic acid based material or HA Types 1-4. Particularly, the viscosity of Compositions 1-7 are significantly lower than the viscosity of the pure tissue matrix particles. The G" value for Compositions 1-7, as shown, are less than 600 Pa, with some of the compositions having G" values less than 500 Pa.

Figure 5:
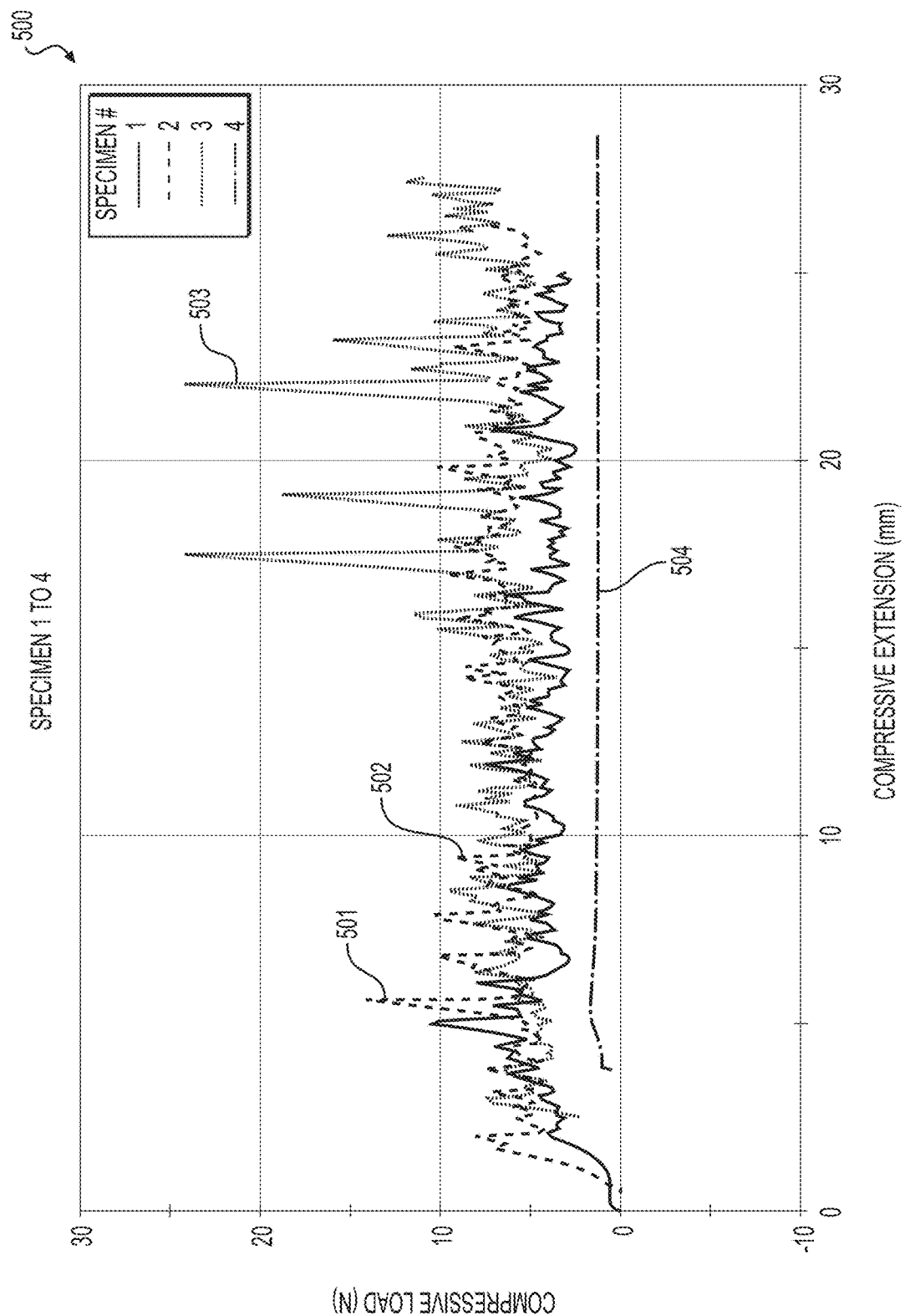
FIG. 5 is a graph illustrating compressive extension and load behavior for known tissue product compositions compared to an exemplary embodiment of a tissue product composition formed in accordance with the present invention.

FIG. 5 illustrates a graph 500 showing compressive load as a function of compressive extension for various tissue product compositions injected using a syringe with an 18 gauge needle. As can be seen, the load vs. extension plots 501, 502, 503 for various injections of pure acellular tissue matrix particles all have large degrees of compressive load fluctuation during the injection and peak compressive loads above 10N during the injection. In contrast, load vs. extension plot 504 for an injection of a tissue product composition comprising acellular tissue matrix particles mixed with HA Type 1 in an ADM:HA ratio of 9:1, i.e., the tissue product composition is 90% acellular tissue matrix particles and 10% flowable carrier, has a relatively constant and low compressive load during the injection. It should therefore be appreciated that mixing the acellular tissue matrix particles with the flowable carrier can both reduce the peak compressive loads on the tissue matrix particles during injection and make the injection "smoother."

Figure 6:
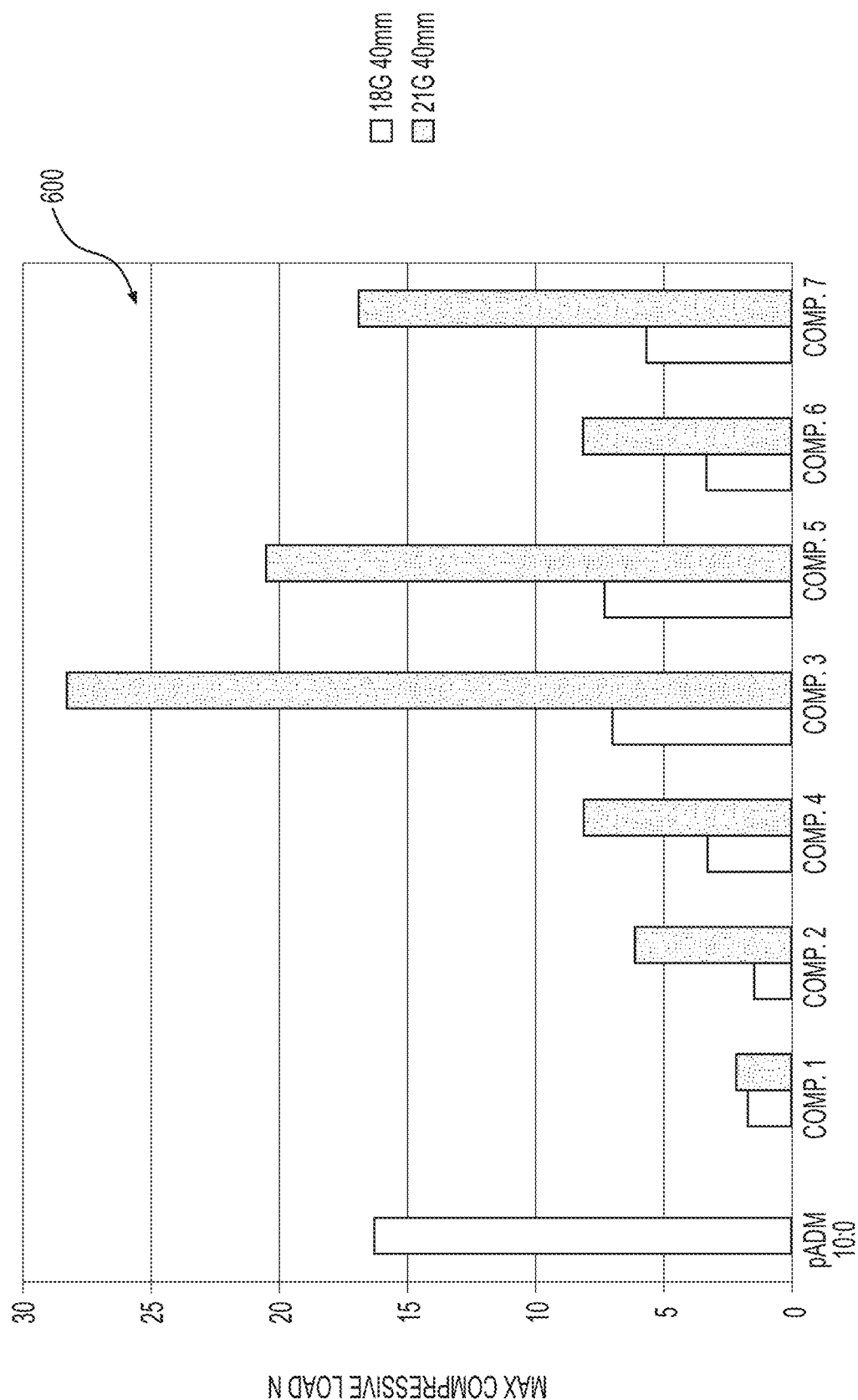
FIG. 6 is a graph illustrating injection forces using different needle sizes for various tissue product compositions.

Referring to FIG. 6, a graph 600 illustrates maximum compressive loads for various tissue product compositions injected through an 18 gauge needle and, where feasible, through a 21 gauge needle. Each trial placed 1 mL of tissue product composition in a reservoir for injection through an 18 gauge or 21 gauge needle by depressing a plunger, with the plunger being depressed a total of 40 mm at a speed of 1 mm/sec. As is known, a 21 gauge needle has a significantly reduced inner diameter compared to an 18 gauge needle. The maximum compressive load for an 18 gauge needle is shown on the left for each material, while the maximum compressive load for a 21 gauge needle is shown on the right for each material; a maximum compressive load for injection of pure acellular tissue matrix through a 21 gauge needle is not shown because the particles are generally too large to pass through a 21 gauge needle in pure form. As can be seen in FIG. 6, the maximum compressive load for injecting pure acellular tissue matrix particles through an 18 gauge needle was significantly higher than the maximum compressive load for injecting any one of Compositions 1-7, formed in accordance with the present invention, through an 18 gauge needle. A maximum compressive load for injecting pure acellular tissue matrix particles through a 21 gauge needle is not illustrated. It was found that injecting Compositions 1, 2, 4, and 6 comprising acellular tissue matrix particles and a flowable carrier through a 21 gauge needle produced a lower maximum compressive load than injecting pure acellular tissue matrix particles through a significantly larger 18 gauge needle. Injection of Compositions 3, 5, and 7 was also possible through a 21 gauge needle, although the respective maximum compressive loads were found to be higher than for Compositions 1, 2, 4, and 6. It should therefore be appreciated that mixing acellular tissue matrix particles within a flowable carrier comprising a hyaluronic acid based material can produce a tissue product composition suitable for injection through a 21 gauge needle.

C. The Tissue Product Compositions have Intact Collagen Structure

Referring now to FIGS. 7-15, various microscope images are shown to illustrate the general structure and distribution of various tissue product compositions.

Figure 7:
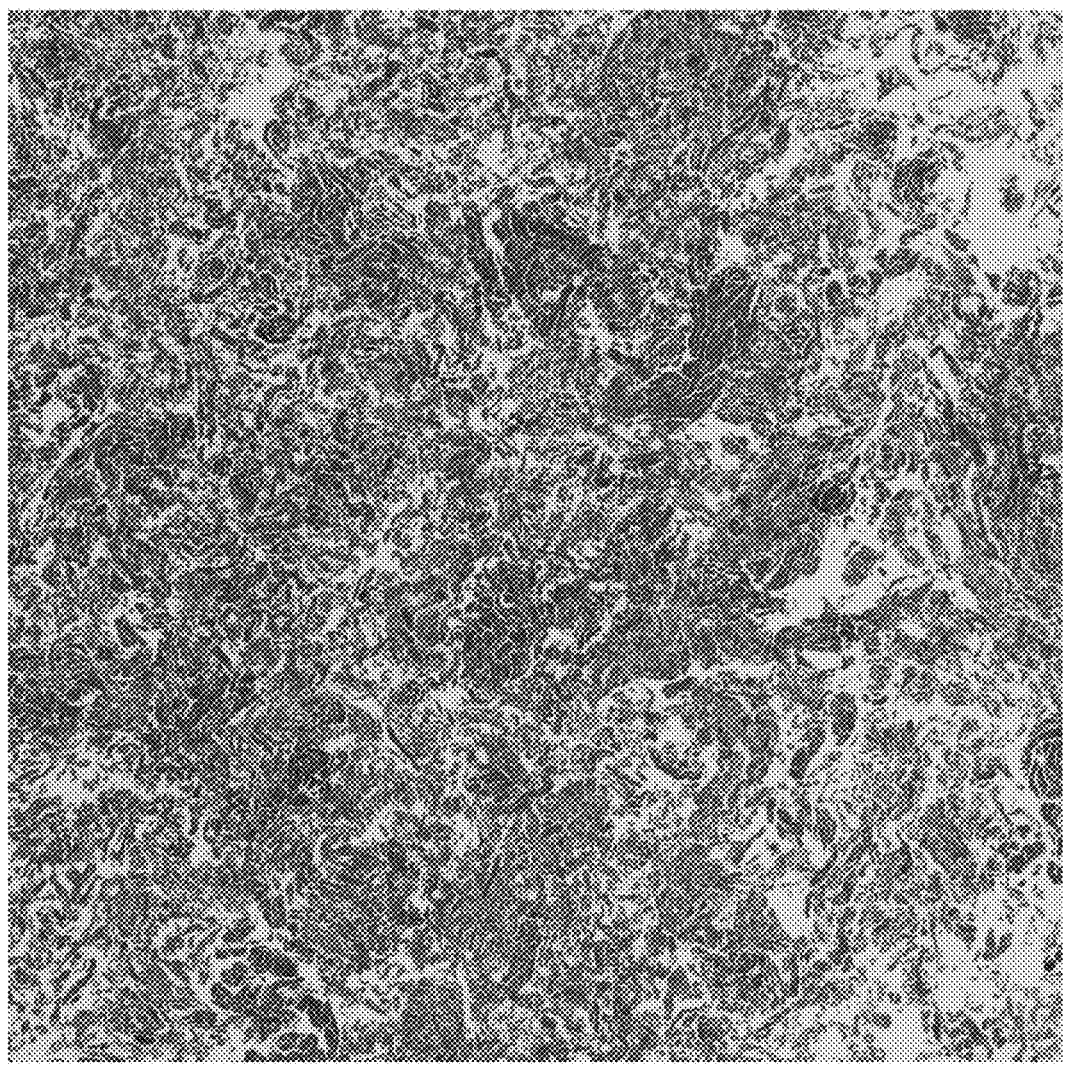
FIG. 7 is a microscope photograph of trichrome stained collagen of an exemplary embodiment of a tissue product composition formed in accordance with the present invention.

Referring specifically to FIG. 7, trichrome staining of a tissue product composition including acellular tissue matrix particles mixed within a flowable carrier comprising a hyaluronic acid based material is shown. As can be seen in FIG. 7, there is no appreciable damage of the collagen fibers and the collagen has normal banding patterns.

Figure 8:
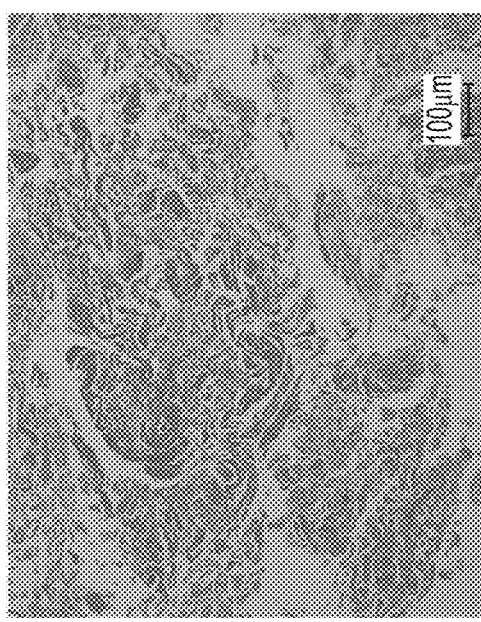
FIG. 8 is a microscope photograph of a tissue product composition comprising acellular tissue matrix particles that are not mixed within a flowable carrier.

Referring specifically to FIG. 8, a microscope image of Haemotoxylin and Eosin (H&E) staining of pure acellular tissue matrix particles is shown. As can be seen, the collagen fibers are normal.

Figure 9:
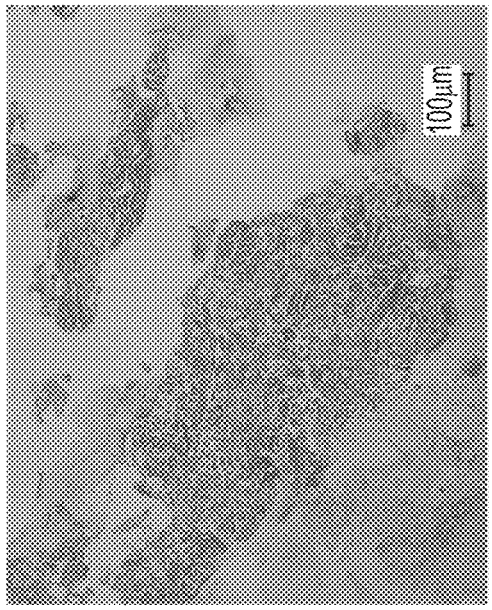
FIG. 9 is a microscope photograph of an exemplary embodiment of a tissue product composition comprising acellular tissue matrix particles that are mixed with a flowable carrier in accordance with the present invention.

Referring specifically to FIG. 9, a microscope image of H&E staining of a tissue product composition including a 5:5 ratio of acellular tissue matrix particles to carrier HA4 is shown. As can be seen, the collagen fibers are normal and the HA4 molecules tend to congregate about the peripheries of the particles.

Figure 10:
FIG. 10 is a microscope photograph of another exemplary embodiment of a tissue product composition formed in accordance with the present invention.

Referring specifically to FIG. 10, a microscope image of H&E staining of a tissue product composition including a 9:1 ratio of acellular tissue matrix particles to carrier HA2 is shown. As can be seen, the collagen fibers are normal and the HA2 molecules tend to be interspersed between the particles.

Figure 11:
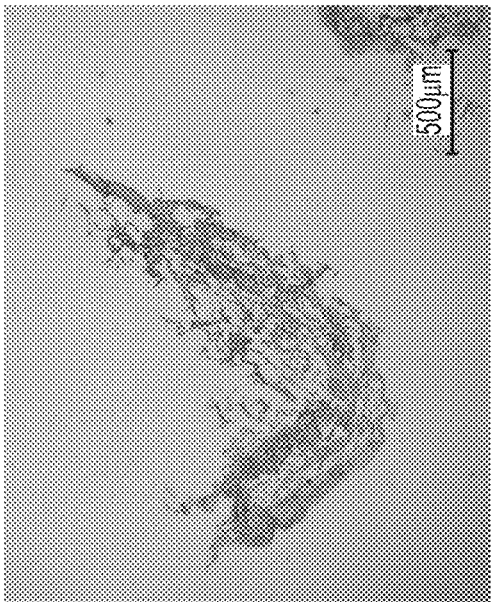
FIG. 11 is a microscope photograph of yet another tissue product composition formed in accordance with the present invention.

Referring specifically to FIG. 11, a microscope image of H&E staining of a tissue product composition including a 1:9 ratio of acellular tissue matrix particles to carrier HA3 is shown. As can be seen, the collagen fibers are normal and the HA3 molecules surround the particles.

Figure 12:
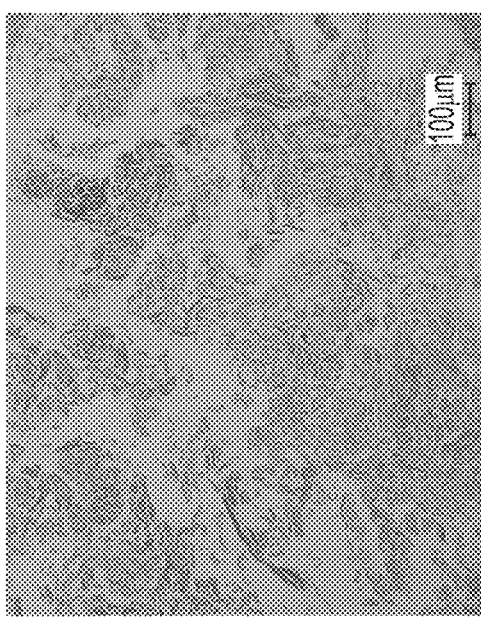
FIG. 12 is a microscope photograph of yet another tissue product composition formed in accordance with the present invention.

Referring specifically to FIG. 12, a microscope image of Alcian Blue staining of pure acellular tissue matrix particles is shown. As can be seen, the collagen fibers are normal.

Figure 13:
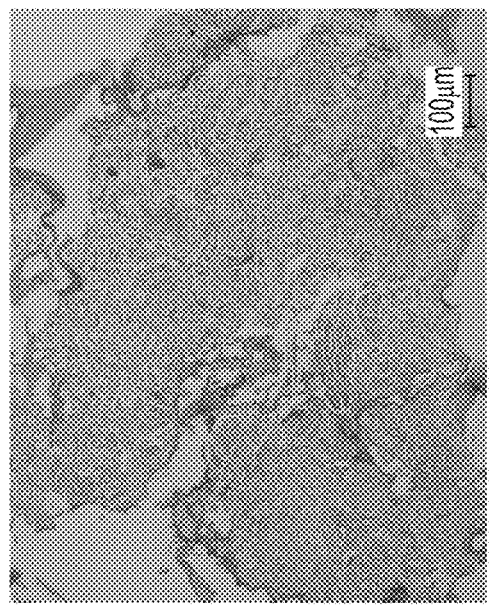
FIG. 13 is a microscope photograph of yet another tissue product composition formed in accordance with the present invention.

Referring specifically to FIG. 13, a microscope image of Alcian Blue staining of a tissue product composition including a 5:5 ratio of acellular tissue matrix particles to carrier HA4 is shown. As can be seen, the collagen fibers are normal and the HA4 molecules tend to congregate about the peripheries of the particles.

Figure 14:
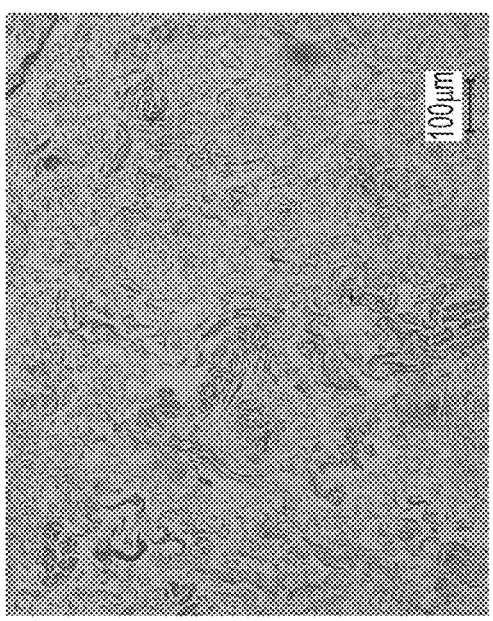
FIG. 14 is a microscope photograph of yet another tissue product composition formed in accordance with the present invention.

Referring specifically to FIG. 14, a microscope image of Alcian Blue staining of a tissue product composition including a 9:1 ratio of acellular tissue matrix particles to carrier HA2 is shown. As can be seen, the collagen fibers are normal and the HA2 molecules tend to be interspersed between the particles.

Figure 15:
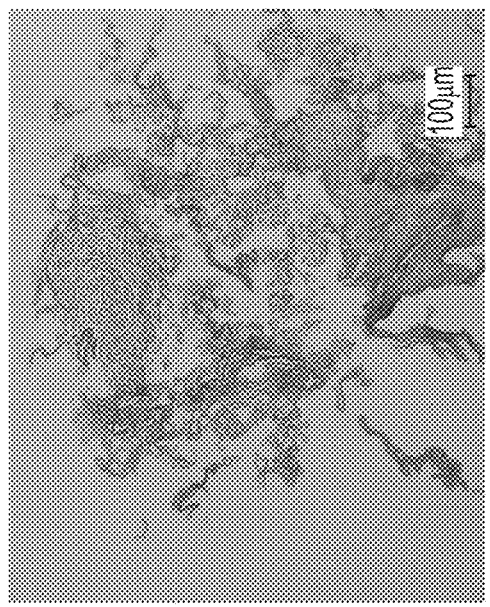
FIG. 15 is a microscope photograph of yet another tissue product composition formed in accordance with the present invention.

Referring specifically to FIG. 15, a microscope image of Alcian Blue staining of a tissue product composition including a 1:9 ratio of acellular tissue matrix particles to carrier HA3 is shown. As can be seen, the collagen fibers are normal and the HA3 molecules surround the particles.

It should therefore be appreciated that tissue product compositions including a flowable carrier comprising a hyaluronic acid based material and acellular tissue matrix particles mixed within the carrier can have suitable structure for supporting tissue growth.

D. In Vivo Implantation of the Tissue Product Compositions Using Hyaluronic Acid (HA) as a Carrier The disclosed tissue product compositions using hyaluronic acid (HA) as a flowable carrier have certain advantages when used as in vivo implants in a host dermal tissue.

Figure 16:
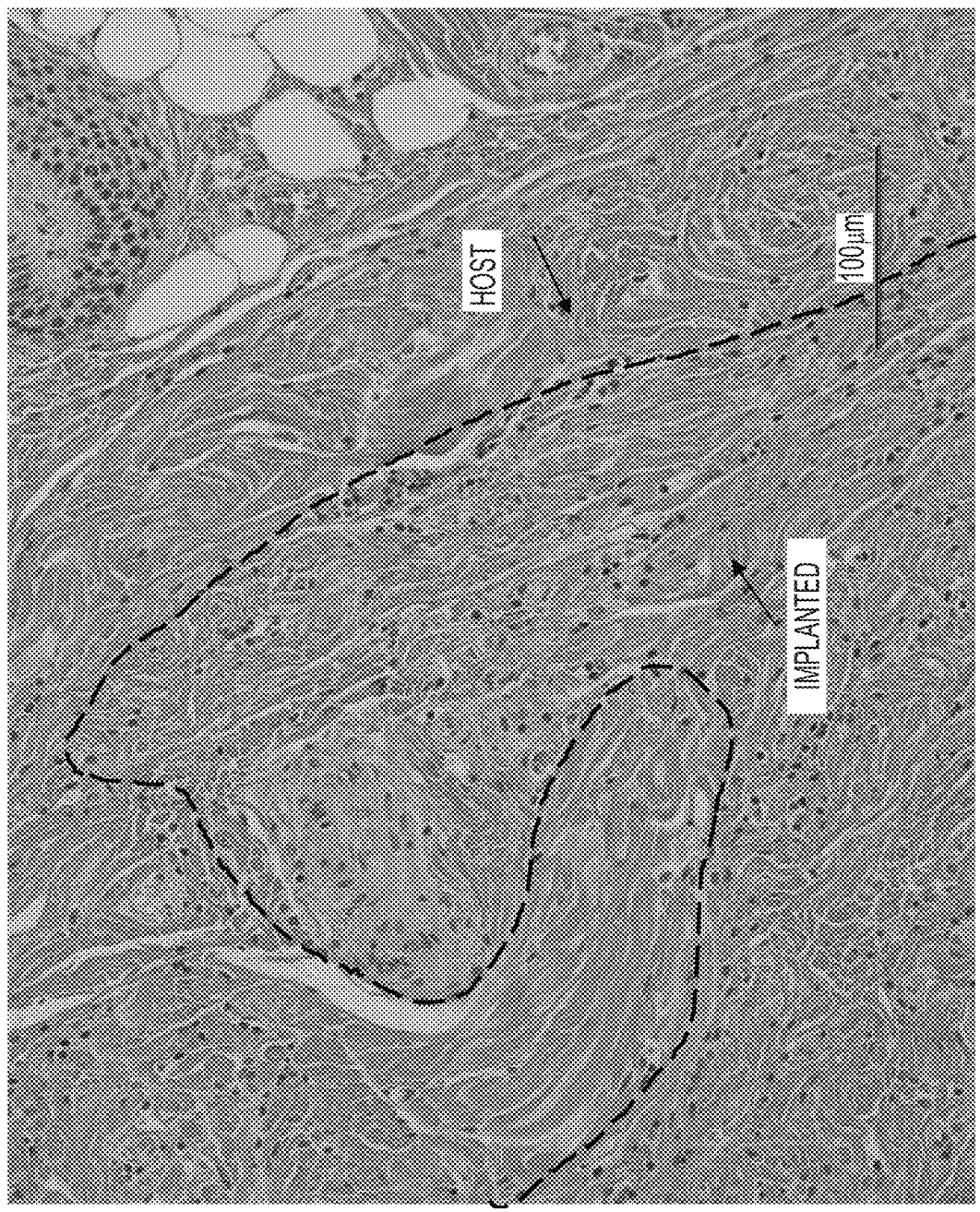
FIG. 16 is a microscope photograph illustrating the integration of a tissue product composition into host dermal tissue four weeks post implantation.

Referring specifically to FIG. 16, acellular tissue matrix particles (15% solid content) were mixed with a 20 mg/mL (2%) non-crosslinked HA carrier in a 19:1 volume ratio. The final solid content of the acellular tissue matrix particles was 14.25%, and the final concentration of the HA carrier was 0.1%. For tissue implantation, 120 µL of the mixture was injected into the subdermal space between the dermis and muscle layers of a rat's dorsal area. Five rats were tested with 4 testing arms each. An explantation was performed 4 weeks post implantation, and the explant was placed in 15 mL of 10% formalin for histology processing followed by an H&E staining. Images were taken under 20× magnification. As shown in FIG. 16, the implanted tissue product with HA as a carrier integrated well into the host dermal tissue 4 weeks post implantation. Notable cellular infiltration with fibroblasts and vascularization occurred with little or no inflammation.

Referring to FIG. 17, the biological responses in tissue implants with or without HA as a carrier were tested. Acellular tissue matrix particles with a 15% solid content was used. When using HA as a carrier, the acellular tissue matrix was mixed with a 20 mg/mL (2%) non-crosslinked HA carrier in a 9:1 volume ratio. The final solid content of the acellular tissue matrix particles was 13.5% and the final concentration of HA was 0.2%. For tissue implantation, 500 µL of acellular tissue matrix particles alone, or the mixture of acellular tissue matrix particles with HA as a carrier was injected subcutaneously into a rat's dorsal area. Five rats were tested with 4 testing arms each. An explantation was performed 4 weeks or 12 weeks post implantation, and the explants were placed in 15 mL of 10% formalin for histology processing followed by an H&E staining. Images were taken under 10 OX magnification. Biological responses such as cell infiltration, vascularization, and minimal inflammation were examined. As shown in FIGS. 17A-D, similar biological responses were observed in tissue explants with the acellular tissue matrix alone, and the acellular tissue matrix with HA as a carrier. These results demonstrate that using HA as a carrier does not adversely impact the host's biological responses to the tissue implants, and the results last for at least 12 weeks post implantation.

Figure 18B:
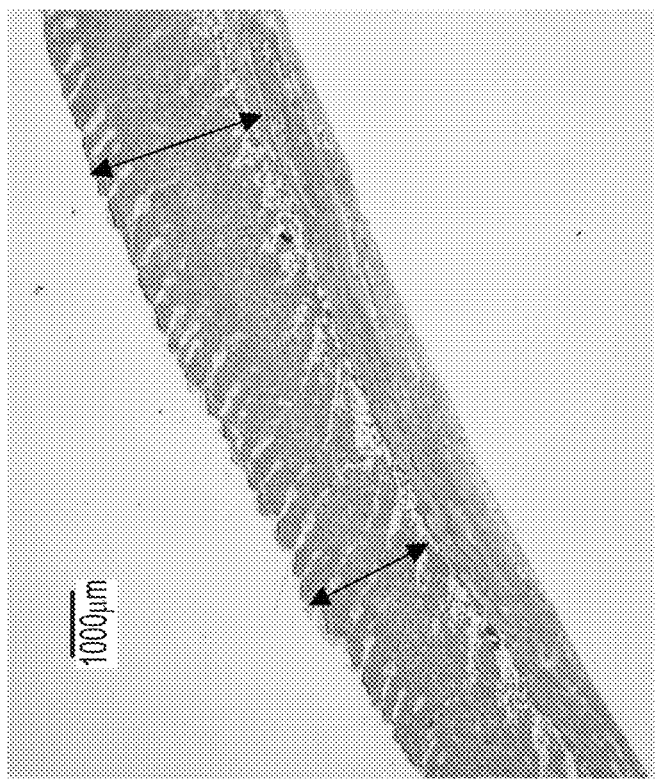
FIGS. 18A and 18B are microscope photographs comparing dermal thickness post-implantation over time.
Figure 18A:
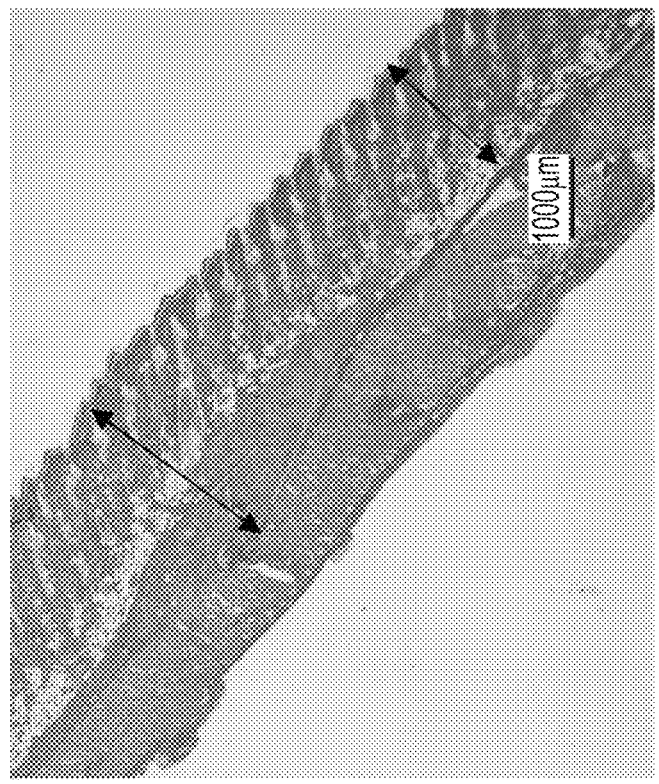

Referring specifically to FIGS. 18A and 18B, increase of dermal thickness in implanted area was tested. Acellular tissue matrix particles (15% solid content) were mixed with a 20 mg/mL (2%) non-crosslinked HA carrier in a 19:1 volume ratio. The final solid content of the acellular tissue matrix particles was 14.25% and the final concentration of the HA carrier was 0.1%. For tissue implantation, 120 µL of the mixture was injected into the subdermal space between the dermis and muscle layers of a rat's dorsal area. Five rats were tested with 4 testing arms each. An explantation was performed 4 weeks or 12 weeks post implantation, and the explants were placed in 15 mL of 10% formalin for histology processing followed by an H&E staining. As shown in FIG. 18, the implantation of the acellular tissue matrix with HA as a carrier significantly increased the thickness of the dermal tissue, and the increase in dermal thickness lasts as long as 12 weeks post implantation (FIG. 18B).

E. Volume Retention of Implanted Tissue Product Compositions

Figure 19:
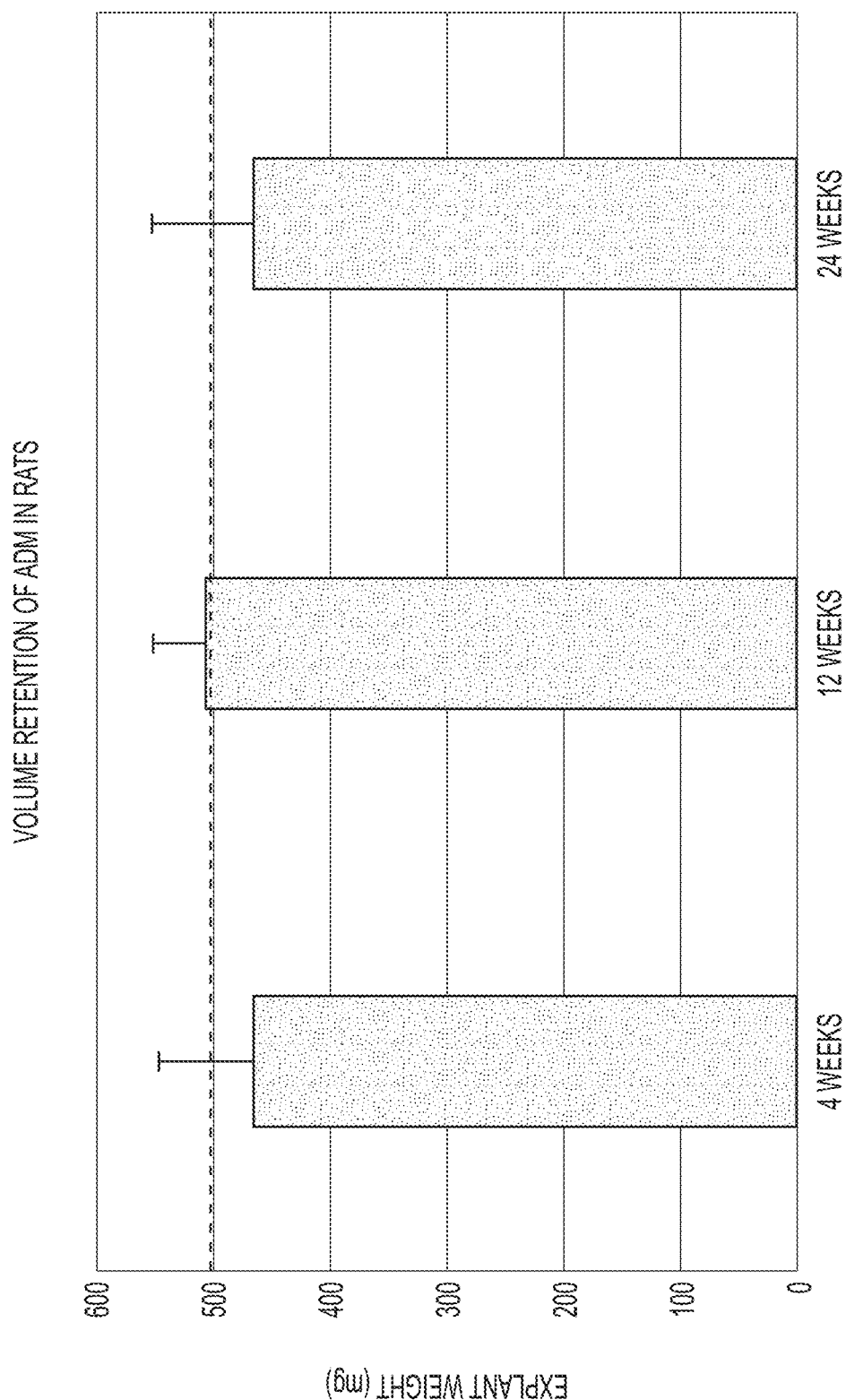
FIG. 19 is a graph illustrating volume retention of implanted tissue product compositions.

Referring specifically to FIG. 19, volume retention of the implanted acellular tissue matrix was tested. For tissue implantation, 500 µL of acellular tissue matrix particles (15% solid content) were injected subcutaneously into a rat's dorsal area. An explantation was performed 4 weeks, 12 weeks, or 24 weeks post implantation. For the 4-week explantation, 10 rats were tested with 4 testing arms each. For the 12-week and 24-week explantations, 5 rats were tested for each group with 4 testing arms in each rat. Explants were harvested and weighted. As shown in FIG. 19, the implanted acellular tissue matrix retained at least 90% of its original volume (dotted line) well for at least 24 weeks post implantation.

Figure 20:
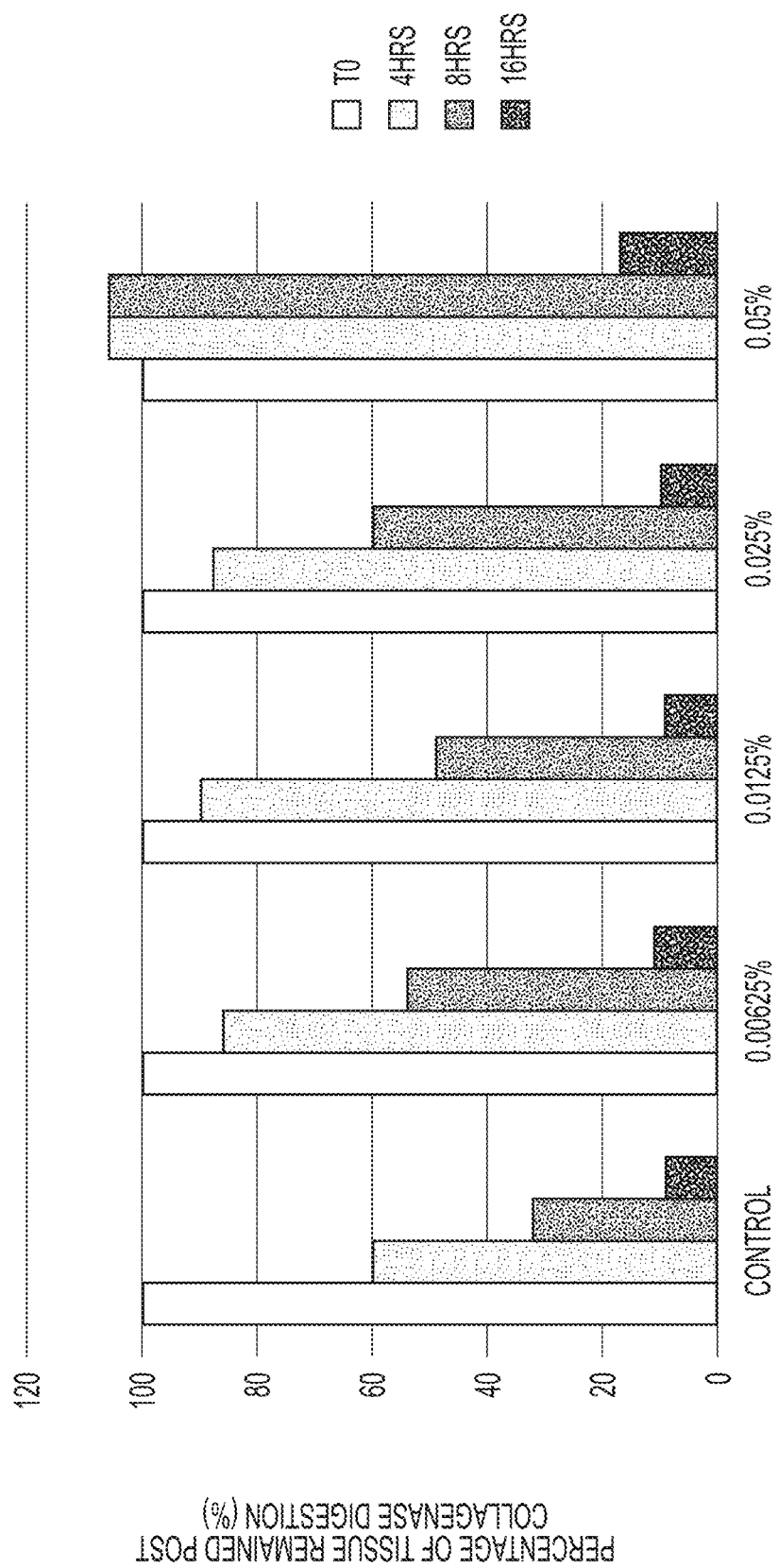
FIG. 20 is a graph illustrating the collagenase resistance of cross-linked tissue product compositions.

Referring specifically to FIG. 20, the acellular tissue matrix particles was treated with different concentrations of 1-ethyl-3-(3-dimethylaminopropyl) carbodiimide hydrochloride (EDC) (0.00625%, 0.0125%, 0.025%, and 0.05%) for 18 hours to form cross-linked tissue products. The cross-linked products were subjected to a final sterilization and washed with PBS for 3 times, 30 min each. Tube weight and wet tissue weight were recorded before the tissues were treated with 1250 U/mL collagenase for 4 h, 8 h, and 16 h, respectively. Triplet samples were tested for each condition. After incubation, the remaining tissues were dried overnight and the weight of the dried tissues in the tube were recorded. The ratios of weight for the dried tissues over the wet tissues before enzymatic treatment were calculated for each time point. As shown in FIG. 20, the cross-linked acellular tissue matrix had significantly increased collagenase resistance compared to non-crosslinked acellular tissue matrix. Higher concentrations of the cross-linker resulted in higher collagenase resistance for the same period of incubation.

Figure 21:
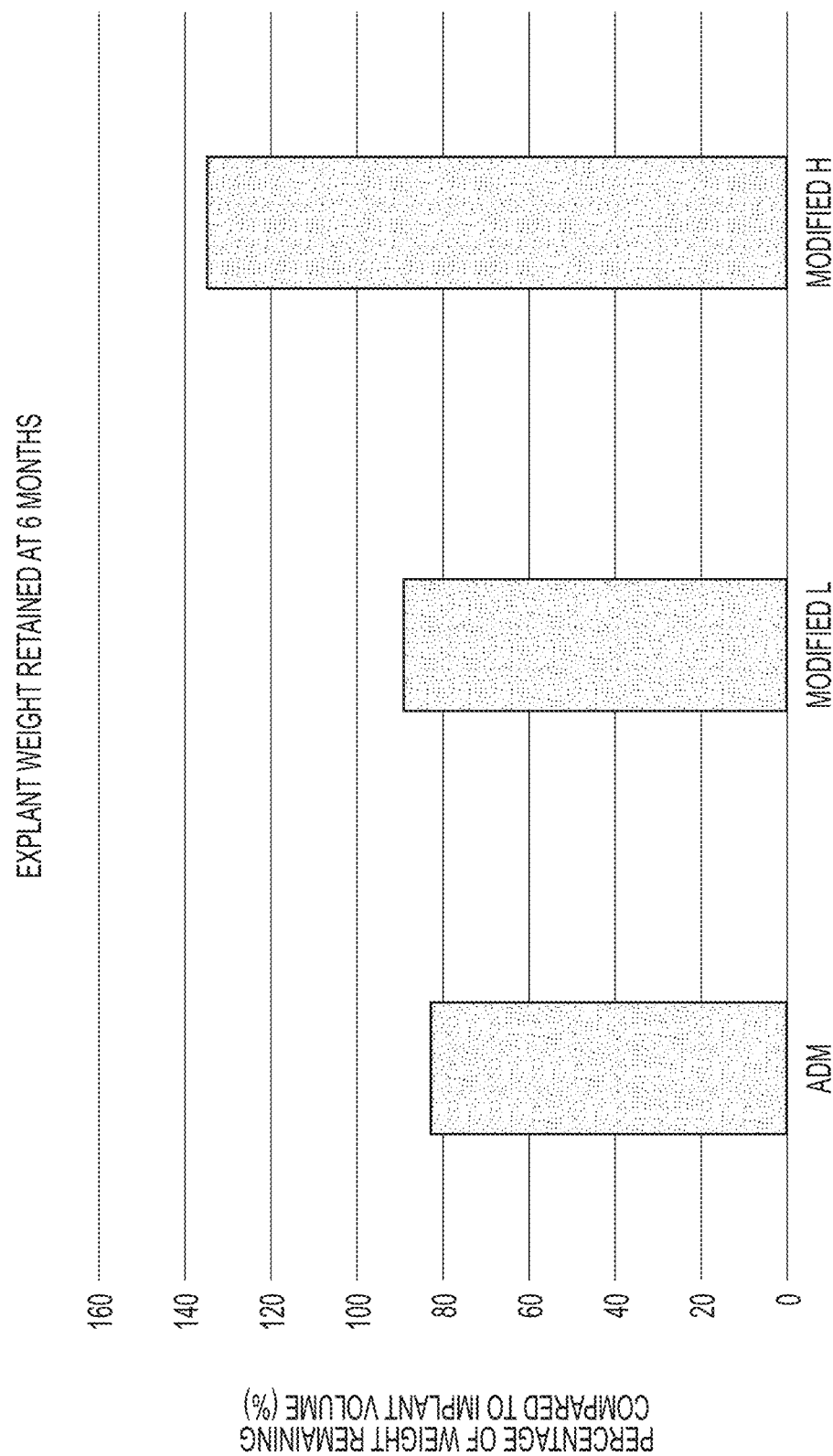
FIG. 21 is a graph illustrating the volume retention of implanted cross-linked tissue product compositions cross-linked using different concentrations of EDC.
Figure 22:
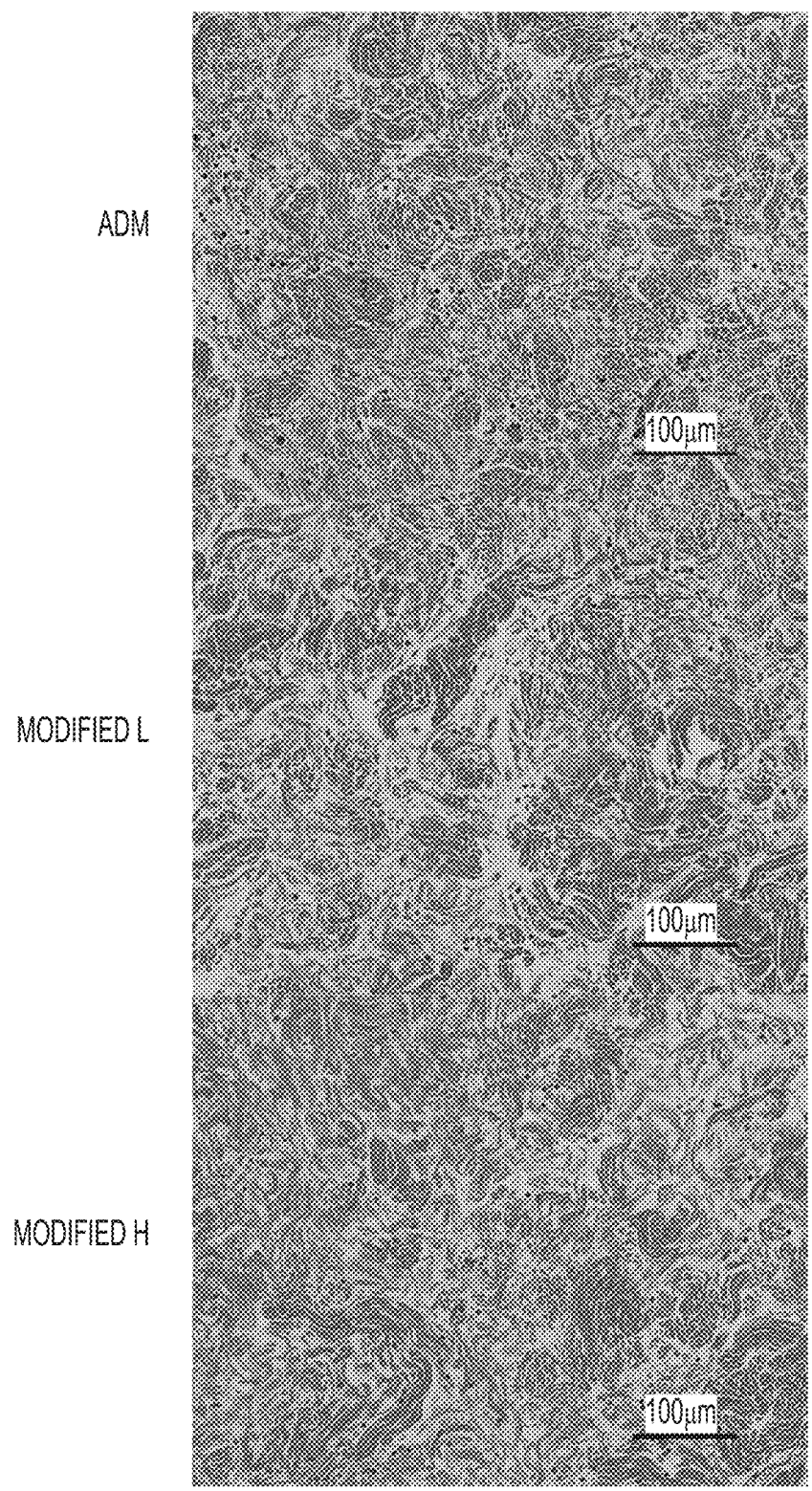
FIG. 22 is a graph illustrating the biological responses in implanted cross-linked tissue product compositions cross-linked using different concentrations of EDC.

Referring specifically to FIGS. 21 and 22, cross-linked acellular tissue matrices were tested for in vivo implantation. 500 µL of acellular tissue matrix particles (15% solid content) were cross-linked with 0.0125% (modified L) or 0.05% (modified H) EDC, respectively, and injected subcutaneously into a rat's dorsal area. Five rats were tested for each condition, with 4 testing arms in each rat. An explantation was performed 4 weeks or 24 weeks post implantation. Explants were harvested and weighted. The harvested explants were stained by H&E staining and representative images were taken under 20× magnification. As shown in FIG. 21, the volumes of the implanted tissue matrices were maintained well for at least 24 weeks, and higher level of cross-linking resulted in better retention of volume. As shown in FIG. 22, similar biological responses were observed in explants with unmodified, modified L, and modified H tissue matrices.

F. Exemplary Uses of the Tissue Product Composition

In one exemplary embodiment provided in accordance with the present invention, a tissue product composition including a flowable carrier comprising a hyaluronic acid based material and acellular tissue matrix particles mixed within the carrier may be loaded into a syringe to form an injection device. In some exemplary embodiments, the tissue product composition may be any of the previously described tissue product compositions. The syringe generally includes a reservoir defining a volume and a needle fluidly coupled to the reservoir. The tissue product composition is held in the reservoir, and in some exemplary embodiments may entirely fill the volume of the reservoir, which may be any desired volume, such as between 0.5 mL and 5 mL. For certain procedures, a reservoir with a considerably larger volume, such as 200 mL, may be used. The inner diameter of the needle may be selected, as desired, according to the injection site and procedure being performed. In some exemplary embodiments, the needle may be an 18 gauge needle, a 19 gauge needle, a 20 gauge needle, a 21 gauge needle, or a higher gauge (lower inner diameter) needle. The injection device may be pre-filled with the tissue product composition and kept in storage prior to being injected.

Alternatively, the injection device may be formed during the procedure by a user, such as a physician, by loading the tissue product composition into an empty syringe. Further, the disclosed compositions can be provided as a kit, wherein the tissue matrix particles are held in a container separate from the carrier or HA component, and a user may mix the component prior to use. The kit can include two or more syringes, two or more vials, a vial/syringe combination, or a multi-compartment system that allows easy mixing at the time of use. It should be appreciated that while the injection device is described as a syringe, the injection device may take other forms suitable for injecting the tissue product composition into a patient.

In one exemplary embodiment provided in accordance with the present invention, a method of treating a patient is provided. The method includes injecting a tissue product composition into a body of the patient, the tissue product composition including a flowable carrier comprising a hyaluronic acid based material and acellular tissue matrix particles mixed within the carrier. In some exemplary embodiments, the tissue product composition may be any of the previously described tissue product compositions. For cosmetic treatments, the tissue product composition may be an injectable composition that is injected into one or more layers the skin of the patient to, for example, reduce the appearance of wrinkles or other lines in the skin. Further, in other exemplary embodiments, the tissue product composition may be formed as a paste or putty that can be applied to other anatomical locations in the patient to restore and/or repair large volumes of lost and/or damaged tissue. It should therefore be appreciated that the tissue product compositions formed in accordance with the present invention can be tailored to many different applications and applied in a variety of different ways.

Figure 23:
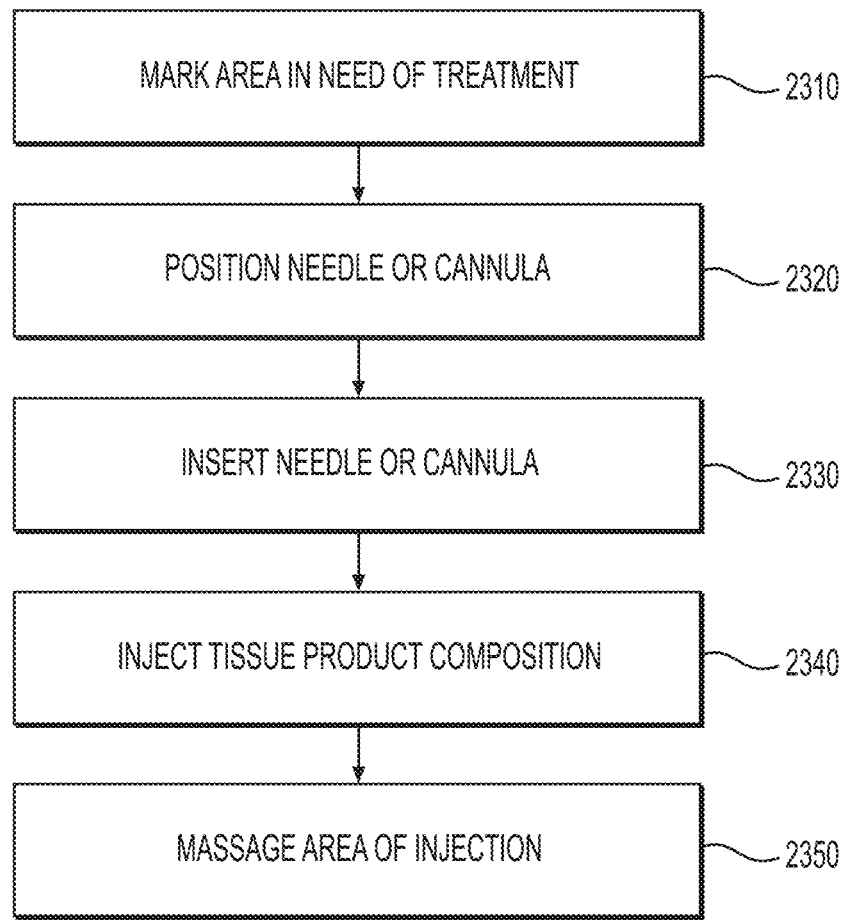
FIG. 23 is a flow chart illustrating an exemplary embodiment of a method for injecting tissue products provided in accordance with the present invention into a hand.

Referring now to FIG. 23, an exemplary embodiment of a method 2300 for injecting a tissue product composition into a hand in accordance with the present invention is illustrated. The method 2300 generally injecting a hand with a plurality of acellular tissue matrix particles within a flowable carrier comprising a hyaluronic acid based material that is loaded within a syringe. In some exemplary embodiments, the method 2300 may also include marking 2310 areas of the hand in need of treatment, for example filling with a tissue filler. For example, a medical professional may circle or otherwise demarcate any the skin of an area of the hand with a marker, pen, or other marking implement. In some embodiments, interosseous spaces of the hand may be marked with a triangle.

The method may continue by positioning 2320 a needle or cannula fluidly coupled to a reservoir holding the tissue product composition relative to the marked area. For example, the tip of the needle or cannula may be positioned at the distal end of the marked area, i.e. closest to the fingertips. As a further example, the tip of the needle or cannula may be positioned at the distal corner of a marked triangular area to produce a fan-shaped distribution of tissue product composition.

The tip of the needle or cannula is then inserted 2330 into the marked area. In some embodiments, the tip is inserted below the undersurface of the dermal layer of the hand. In further embodiments, the lateral hole of the tip is oriented upwards towards the undersurface of the dermal layer. In some embodiments, an incision is made into the skin to allow for insertion of the tip of the needle or cannula. In further embodiments, a crescent-shaped incision is made.

After insertion of the tip of the needle or cannula the housed tissue product composition is injected 2340 into the marked area. In some embodiments, the composition is inserted between the dermal layer and the fascia layer of the hand. The composition may be inserted using a scraping technique where the tip of the needle or cannula scrapes along the undersurface of the dermal layer as the tip is moved through the marked area. In some embodiments, the tip of the needle or cannula is moved through the marked area from the same entry point to distribute the tissue product composition in a fan-shaped disbursement.

Optionally, injection may be followed by massaging 2350. In some embodiments, the injected composition can be manually massaged to further spread the composition throughout the marked area. Massaging may include the application of pressure with a medical professional's hand(s) or with an implement. Massaging includes any action that causes movement of the tissue product composition within the marked area to spread the tissue product composition.

In some embodiments, multiple injections are made to treat an area. For example, steps 2320-2340 may be repeated until a sufficient amount of tissue product composition is administered to the area identified for treatment. Massaging step 2350 may also be repeated as necessary.

Figure 24:
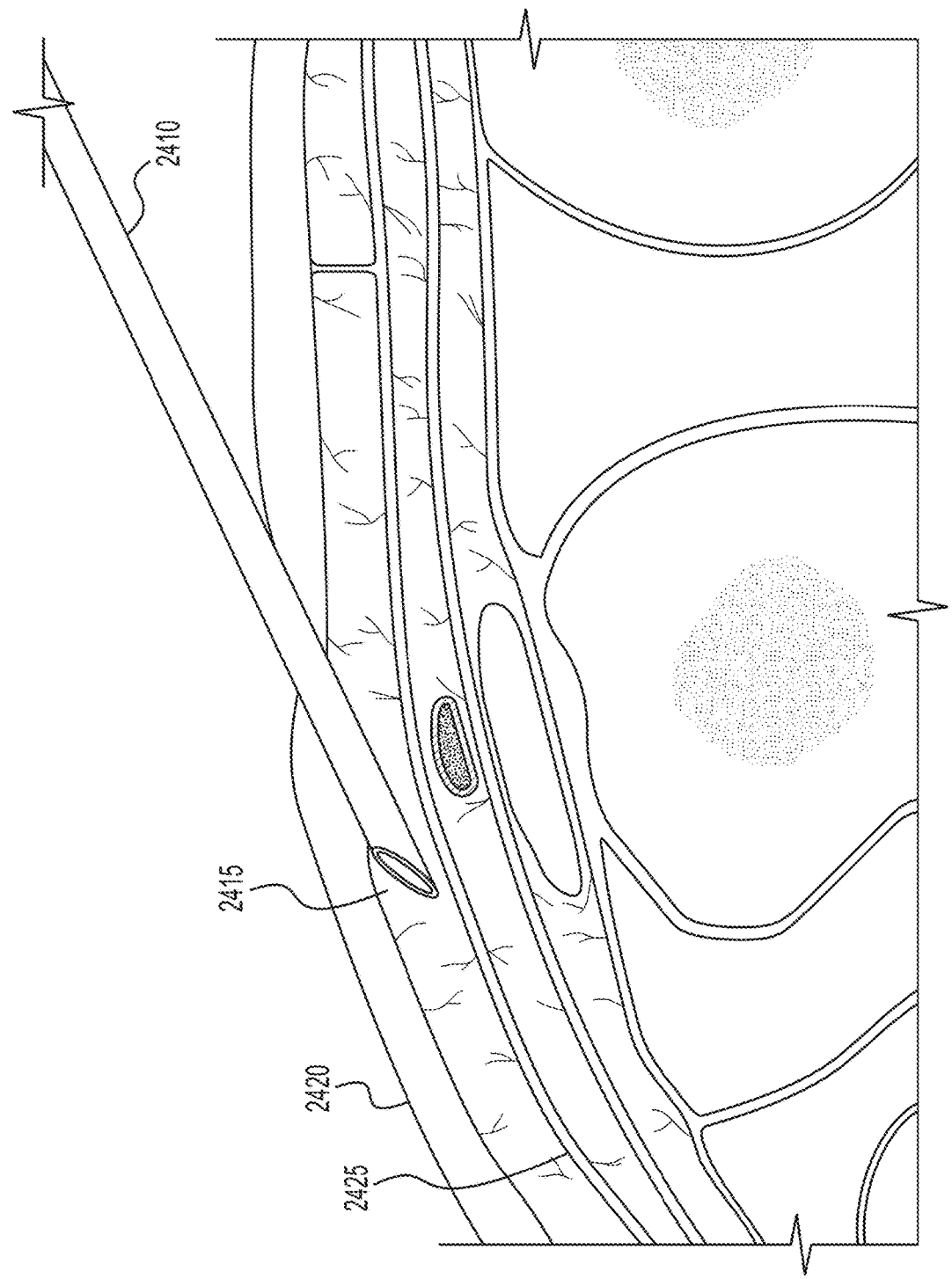
FIG. 24 depicts the injection of tissue products into a hand according to certain embodiments.

FIG. 24 depicts a needle or cannula delivering a tissue product composition into a hand. The needle or cannula 2410 may be inserted into the hand by a medical professional. The needle or cannula 2410 may be soft-tipped, blunt, and/or round-tipped. The bevel 2415 of the needle or cannula 2410 should be facing the underside of the hand to allow for easier guidance of the needle or cannula 2410 into the hand.

In some embodiments, the medical professional engages the skin of the hand to allow for insertion of the tip of the needle or cannula 2410 into the area between the dermal layer and the fascia layer of the hand. For example, the medical professional may pinch and lift up the skin of the hand.

The injected tissue product composition provides an improved spreadability as compared to acellular tissue matrix particles alone. In some embodiments, the injected tissue product composition requires less massaging to pervade through a treated area than acellular tissue matrix particles alone. In some embodiments, the tissue product composition requires no massaging to sufficiently spread through a treatment area.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

What is claimed is:

1. A method of treating a hand, comprising:
identifying at least one area of a hand to be treated;
inserting a tip of a needle or cannula fluidly coupled to a reservoir defining a volume into the at least one area, the reservoir holding a tissue product composition, comprising:
a flowable carrier comprising a hyaluronic acid based material; and
a plurality of dermal acellular tissue matrix particles mixed within the carrier; and
injecting the composition between a dermal layer and a fascia layer of the at least one area to cause cellular ingrowth thereby increasing the thickness of the dermal layer.

2. The method of claim 1, wherein identifying the at least one area of the hand to be treated comprises marking at least one interosseous area of the hand.

3. The method of claim 1, wherein the tip of the needle or cannula is inserted below an undersurface of the dermal layer.

4. The method of claim 3, wherein a tip of the needle or cannula scrapes the undersurface of the dermal layer.

5. The method of claim 1, further comprising massaging the at least one area to further spread the composition.

6. The method of claim 1, wherein the tip of the needle or cannula is soft-tipped.

7. The method of claim 1, wherein the hyaluronic acid based material is a cross-linked hyaluronic acid.

8. The method of claim 1, wherein the hyaluronic acid based material is a non-cross-linked hyaluronic acid.

9. The method of claim 1, wherein the carrier has a concentration of about 20 mg/mL hyaluronic acid prior to mixing.

10. The method of claim 1, wherein the tissue matrix particles originate from a dermal matrix and an adipose matrix.

11. The method of claim 1, wherein the composition comprises a volume ratio of tissue matrix to carrier from 1:9 to 19:1.

12. The method of claim 1, wherein the carrier and tissue matrix particles are mixed to form a slurry with about 1.5% to about 14.25% solid content.

13. The method of claim 12, wherein the slurry has a G" value at 5 Hz that is less than 600 Pa.

14. The method of claim 13, wherein the G" value at 5 Hz is less than 500 Pa.

15. The method of claim 1, wherein the composition further comprises a plurality of seed cells intermixed with the carrier and tissue matrix particles.

* * * * *